(12) United States Patent
Gazit et al.

(10) Patent No.: US 9,670,139 B2
(45) Date of Patent: *Jun. 6, 2017

(54) TELOMERASE ACTIVATING COMPOUNDS AND METHODS OF USE THEREOF

(71) Applicant: BEN-GURION UNIVERSITY OF THE NEGEV RESEARCH AND DEVELOPMENT AUTHORITY, Beer Sheva (IL)

(72) Inventors: Aviv Gazit, Jerusalem (IL); Shimon Slavin, Jerusalem (IL); Esther Priel, Beer Sheva (IL); Sara Yitzchak, Tiberias (IL)

(73) Assignee: BEN-GURION UNIVERSITY OF THE NEGEV RESEARCH AND DEVELOPMENT AUTHORITY, Beer Sheva (IL)

( * ) Notice: Subject to any disclaimer, the term of this patent is extended or adjusted under 35 U.S.C. 154(b) by 29 days.

This patent is subject to a terminal disclaimer.

(21) Appl. No.: 14/109,309

(22) Filed: Dec. 17, 2013

(65) Prior Publication Data

US 2014/0142068 A1 May 22, 2014

Related U.S. Application Data

(62) Division of application No. 12/602,956, filed as application No. PCT/IL2008/000756 on Jun. 4, 2008, now Pat. No. 8,609,736.

(60) Provisional application No. 60/924,875, filed on Jun. 4, 2007, provisional application No. 60/929,524, filed on Jul. 2, 2007, provisional application No. 60/929,525, filed on Jul. 2, 2007, provisional application No. 61/006,924, filed on Feb. 6, 2008.

(51) Int. Cl.
| | |
|---|---|
| *C07C 215/80* | (2006.01) |
| *A61K 31/03* | (2006.01) |
| *A61K 31/05* | (2006.01) |
| *A61K 31/055* | (2006.01) |
| *A61K 31/136* | (2006.01) |
| *A61K 31/66* | (2006.01) |
| *A61K 31/695* | (2006.01) |
| *C07C 215/50* | (2006.01) |
| *C07D 213/16* | (2006.01) |
| *C07D 213/30* | (2006.01) |
| *C07D 295/096* | (2006.01) |
| *C07C 43/225* | (2006.01) |
| *C07D 295/135* | (2006.01) |
| *C07C 39/367* | (2006.01) |
| *C07C 43/23* | (2006.01) |
| *C07F 9/50* | (2006.01) |

(52) U.S. Cl.
CPC ............ *C07C 215/80* (2013.01); *A61K 31/03* (2013.01); *A61K 31/05* (2013.01); *A61K 31/055* (2013.01); *A61K 31/136* (2013.01); *A61K 31/66* (2013.01); *A61K 31/695* (2013.01); *C07C 39/367* (2013.01); *C07C 43/225* (2013.01); *C07C 43/23* (2013.01); *C07C 215/50* (2013.01); *C07D 213/16* (2013.01); *C07D 213/30* (2013.01); *C07D 295/096* (2013.01); *C07D 295/135* (2013.01); *C07F 9/5022* (2013.01)

(58) Field of Classification Search
CPC ...... A61K 31/03; A61K 31/05; A61K 31/055; A61K 31/136; A61K 31/66; A61K 31/695; C07C 215/50; C07C 215/80; C07C 39/367; C07C 43/225; C07C 43/23; C07D 213/16; C07D 213/30; C07D 295/096; C07D 295/135; C07F 9/5022

See application file for complete search history.

(56) References Cited

U.S. PATENT DOCUMENTS

| | | | |
|---|---|---|---|
| 4,093,557 A | 6/1978 | Zecher | |
| 4,783,495 A | 11/1988 | Pastor et al. | |
| 4,835,202 A | 5/1989 | Pastor et al. | |
| 5,198,531 A | 3/1993 | Webber | |
| 5,243,018 A | 9/1993 | Kuze et al. | |
| 5,290,658 A | 3/1994 | Uenishi et al. | |
| 5,583,016 A | 12/1996 | Villeponteau et al. | |
| 5,625,027 A | 4/1997 | Kuze et al. | |
| 6,331,564 B1 * | 12/2001 | Brugnara et al. | ............. 514/520 |
| 6,380,378 B1 | 4/2002 | Kitamura et al. | |
| 6,399,738 B1 | 6/2002 | Ito | |
| 7,115,619 B2 | 10/2006 | Stevens et al. | |
| 7,846,904 B2 | 12/2010 | Harley et al. | |
| 8,604,245 B2 | 12/2013 | Priel et al. | |
| 2006/0111365 A1 | 5/2006 | Tauchi | |
| 2007/0042962 A1 | 2/2007 | Adams et al. | |

FOREIGN PATENT DOCUMENTS

| | | |
|---|---|---|
| EP | 2152663 B1 | 3/2014 |
| JP | 02121941 A | 5/1990 |
| JP | 10153884 A | 6/1998 |
| JP | 10273461 A | 10/1998 |

(Continued)

OTHER PUBLICATIONS

Chan et al. (Naunyn-Schmiedeberg's Arch Pharmacol, 1997, 356:763-768).*
Peterson et. al. "Expanding the Scope of Crystal Form Evaluation in Pharmaceutical Science" Journal of Pharmacy & Pharmaceutical Science 2006 (9(3):317-326.*
Morissette et al. Adv. Drug Delivery Rev. 2004, 56,275-300.*
A.M. Rouhi, Chem. & Eng. News, Feb. 24, 2003, 81(8).*
Notice of Allowance, Applicant Initiated Interview Summary, and Notice of Allowability, including PTO-892 and AFCP 2.0 Decision dated Feb. 3, 2017 and issued in connection with U.S. Appl. No. 14/070,073, filed Nov. 12, 2013 (13 pages).

(Continued)

*Primary Examiner* — Uma Ramachandran
(74) *Attorney, Agent, or Firm* — Lucas & Mercanti, LLP

(57) ABSTRACT

The present invention is directed to use of a series of compounds and compositions comprising the same for activating telomerase and treating diseases, disorders and/or conditions related thereto.

5 Claims, 16 Drawing Sheets

(56) References Cited

FOREIGN PATENT DOCUMENTS

| JP | 2005008626 A | 1/2005 |
|---|---|---|
| JP | 2006059694 A | 3/2006 |
| JP | 2007016214 A | 1/2007 |
| JP | 2001312055 A | 11/2011 |
| WO | 9315063 A1 | 8/1993 |
| WO | 01/30771 A1 | 5/2001 |

OTHER PUBLICATIONS

Daniela Cihakova MD., Ph.D., "Type 1 Diabetes Mellitus", Johns Hopkins Medical Institutions Autoimmune Disease Research Center, 2001, Printout dated Jun. 18, 2015 from http:autoimmune.pathology.jhmi.edu/diseases.cfm?systemID=3&DiseaseID=23 (5 pages).
Lomakin et al., "Modern Polymer Flame Retardancy", New Concepts in Polymer Science, 2003 (3 pages).
Canadian Examination Report for related Canadian Patent Application No. 2,690,004, dated Feb. 8, 2016 (3 pages).
West, "Solid State Chemistry and Its Applications," Wiley, 1988 (3 pages).
Dyker et al. "Sterically Stabilized p-Quinodimethanes by Nucleophilic Aromatic Substitution", European Journal of Organic Chemistry, vol. 2006, No. 9, 2006, pp. 2134-2144.
Eurasian Office Action dated Jan. 15, 2016, which is issued for related Eurasian Application No. 201401193/28 and its English translation (5 pages).
Neamati et al., "Depsides and depsidones as inhibitors of HIV-1 integrase: Discovery of Novel Inhibitors through 3D Database Searching," Journal of Medicinal Chemistry, American Chemical Society, 1997, vol. 40, No. 6, pp. 942-951.
N. Dessalew et al., "Investigation of potential glycogen synthase kinase 3 inhibitors using pharmacophore mapping and virtual screening", Chemical Biology & Drug Design, Blackwell Publishing TD., 2006, vol. 68, No. 3, pp. 154-165.
Pastor et al., "Organophosphorous and organosilicon derivatives of sterically hindered phenols", Journal of Organometallic Chemistry, 1989, vol. 376, No. 1, pp. 21-29.
B. Kirste et al., "Hydrogen-1 and Carbon-13 ENDOR investigations of sterically hindered galvinoxyl radicals", Journal of the American Chemical Society, 1981, vol. 103, No. 21, pp. 6280-6286.
M. E. Wacks et al., "Multiply charged ions", Recent Topics in Mass Spectrometry: Articles . . . From a NATO Study Institute of Mass Spectrometry, Gordon and Breach Science Publishers, 1971, pp. 1-9.
PCT International Search Report (as WO 2008/149345 A3) issued in related PCT Application No. PCT/IL2008/000747 filed Nov. 10, 2008 (2 pages).
Extended European Search Report issued in related European Application No. 08763505.8, Oct. 10, 2011 (15 pages).

\* cited by examiner

TELOMERASE ACTIVATING COMPOUNDS AND METHODS OF USE THEREOF

CROSS-REFERENCE TO RELATED APPLICATIONS

This application is a Division of U.S. patent application Ser. No. 12/602,956, filed Jun. 17, 2010, which in turn is a 371 of PCT International Application No. PCT/IL2008/000756, filed Jun. 4, 2008, which claims the benefit of U.S. Provisional Application Nos. 60/924,875, filed Jun. 4, 2007, 60/929,524, filed Jul. 2, 2007, 60/929,525, filed Jul. 2, 2007 and 61/006,924, filed Feb. 6, 2008. The disclosures of all applications are herein incorporated by reference.

FIELD OF THE INVENTION

The present invention is directed to use of a series of compounds and compositions comprising the same for enhancing expression and/or activating telomerase and for treating diseases, disorders and/or conditions related thereto.

BACKGROUND OF THE INVENTION

Telomerase is a ribonucleoprotein that catalyzes the addition of telomeric repeats to the ends of telomeres. Telomeres are long stretches of repeated sequences that cap the ends of chromosomes. In humans, telomeres are typically 7-10 kb in length and comprise multiple repeats. Telomerase is not expressed in most adult cells, and telomere length decreases with successive rounds of replication Telomerase acts as reverse transcriptase in the elongation of telomeres, which prevent the loss of telomeres due to the end replication problems. Without telomerase the telomeres are shortened at each cell division which leads to senescence, apoptosis and cell death caused by chromosome instability. Telomerase is inactive in somatic cells but active in 90% of cancer cells, where telomerase is reactivated. Although telomerase activation may be dangerous, because it can mimic the cancer development process, telomerase enhancing agents may be theoretically applicable as anti-aging agents and clinically useful in certain medical conditions. In contrast, telomerase inhibitors may be useful to fight cancer. Cancer and aging are closely inter-related: Interventions that protect against cancer can lead to premature aging while immortalization of cells is required in the formation of malignant cancer cells. Despite the theoretical risk of activation of carcinogenesis, activation of telomerase may lead to reduced rate of aging.

The assessment of the telomere length is important in the understanding of biological and clinical significance of the telomere. The telomere length serves as a useful indicator in the study of the chromosomal stability, telomerase activity and/or expression, proliferative capacity and aging process of the cells. The clinical value of telomeres can be demonstrated in its importance in cancer, premature aging syndrome or segmental progeria; genetic anomalies, diseases resulting from chromosomal instability, such as Bloom syndrome (a rare inherited disorder characterized by a high frequency of breaks and rearrangements in an affected person's chromosomes), and age-related diseases, such as Warner's Syndrome (a rare illness that manifests rapid aging in younger people). The dynamics of telomere length have distinct patterns of expression in specific disease progressions. Therefore it has a great value in the prognosis of the diseases.

Telomere length can be measured by southern blot, hybridization protection assay, fluorescence in situ hybridization, flow cytometry, primed in situ, quantitative-polymerase chain reaction and single telomere length analysis.

Lack of telomerase activity and/or expression and short telomeres may cause dyskeratosis congenita, aplastic anemia, increase of death due to cardiovascular diseases, strokes or infections, hypertension or chronic stress.

It was shown that transduction of telomerase in telomerase knockout mice prevented damage in the liver.

In addition to the role of telomerase in telomere length maintenance, accumulating data suggest that the telomerase reverse transcriptase (TERT) protein has additional physiological functions, i.e. protecting cells and mice from various damages in a mechanism (yet unclear) that does not involve telomere elongation.

Compounds which activate telomerase will thus find application in multiple clinically relevant scenarios.

SUMMARY OF THE INVENTION

In one embodiment, this invention provides a method of stimulating or increasing telomerase activity and/or expression in a cell or tissue, comprising contacting said cell or tissue with a compound represented by the structure of formula I:

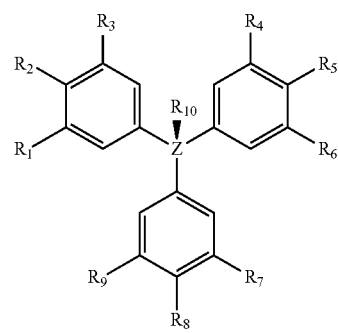

wherein

Z is carbon, nitrogen, phosphorous, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In one embodiment, this invention provides a method of treating a condition capable of being affected by telomerase activation and/or expression in a subject, comprising administering to said subject a compound represented by the structure of formula I:

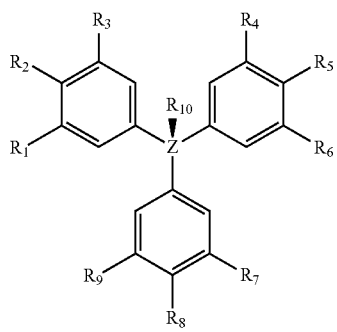

I wherein

Z is carbon, nitrogen, phosphorous, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof; whereby said compound stimulates or enhances telomerase activity and/or expression.

In another embodiment, said condition is HIV infection or a degenerative disease. In another embodiment, said degenerative disease is neurodegenerative disease, a degenerative disease of the bones or joints, macular degeneration, atherosclerosis, or anemia. In one embodiment, said condition is an inflammatory disease. In another embodiment, said condition is dyskeratosis congenita. In another embodiment, the condition is aplastic anemia. In another embodiment, said condition is cancer.

In one embodiment, this invention provides a method of treating an acute or chronic condition of the skin, comprising contacting skin with a compound represented by the structure of formula I:

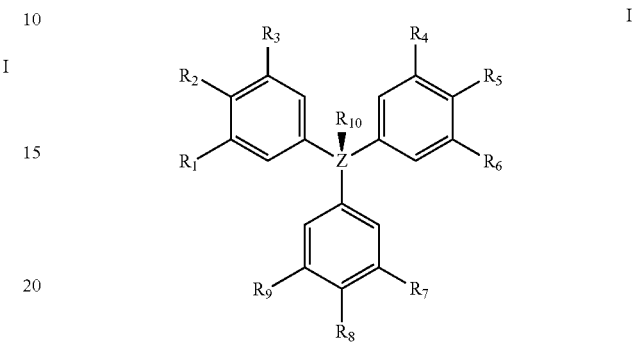

I wherein

Z is carbon, nitrogen, phosphorous, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In another embodiment, said acute or chronic condition is a wound, a burn, an abrasion, an incision, a graft site, a vascular lesion, a lesion caused by an infectious agent, a chronic venous ulcer, a diabetic ulcer, a compression ulcer, a pressure sore, a mucosal sore or ulcer, and keloid formation.

In one embodiment, this invention provides a method of inhibiting, abrogating or delaying cellular senescence in a subject, comprising administering to said subject, a compound represented by the structure of formula I:

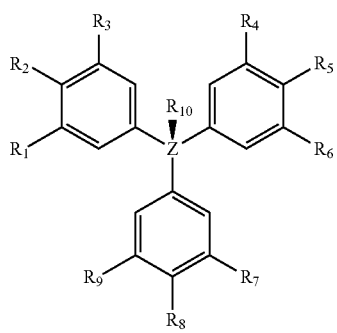

wherein

Z is carbon, nitrogen, phosphorous, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In another embodiment, the method of inhibiting, abrogating or delaying cellular senescence in said subject extends a lifespan in said subject.

In one embodiment, this invention provides a method of diminishing or abrogating the effects of aging in a subject, comprising administering to said subject a compound represented by the structure of formula I:

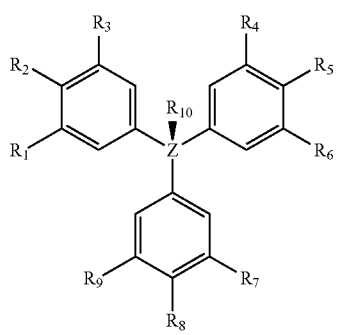

wherein

Z is carbon, nitrogen, phosphorous, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In another embodiment, the effects of aging comprise effects of the skin, eyes, musculature, or bones of the subject.

In another embodiment the structure of formula I is represented by the structure of formula IV:

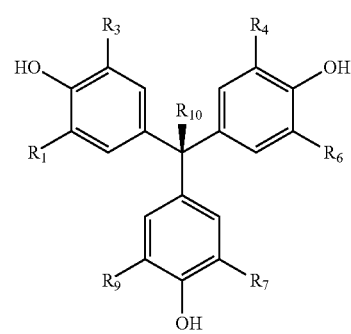

wherein $R_1$, $R_3$, $R_4$, $R_6$, $R_7$, $R_9$ and $R_{10}$ are as described above.

In another embodiment the structure of formula I is represented by the structure of formula VI:

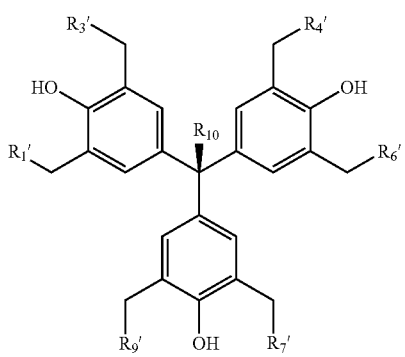

VI wherein $R_1'$, $R_3'$, $R_4'$, $R_6'$ $R_7'$, and $R_9'$ are the same or different comprising halogen, aryl, alkyl, cycloalkyl, heterocycloalkyl, alkoxy, monoalkylamino, dialkylamino or arylamino; and $R_{10}$ is as described above.

In another embodiment the structure of formula I is represented by the structure of formula VII:

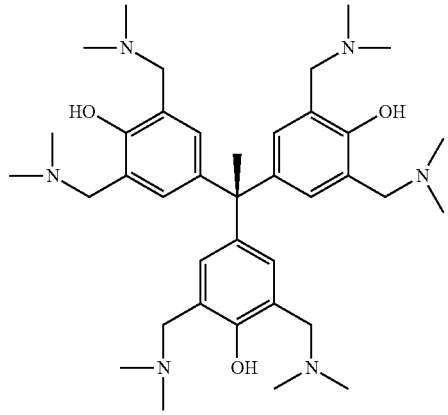

VII

In another embodiment the structure of formula I is represented by the structure of formula VIII:

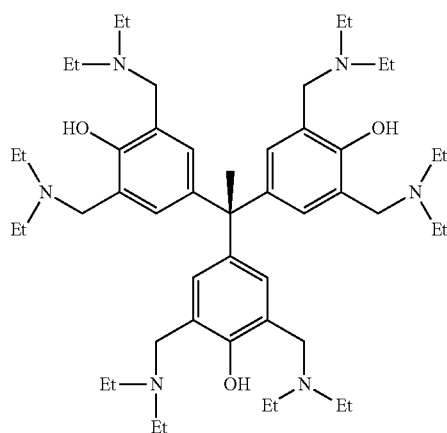

VIII

In another embodiment the structure of formula I is represented by the structure of formula IX:

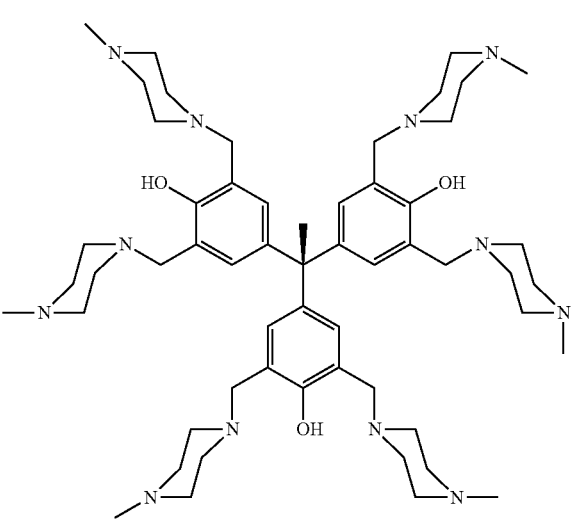

IX

In another embodiment the structure of formula I is represented by the structure of formula X:

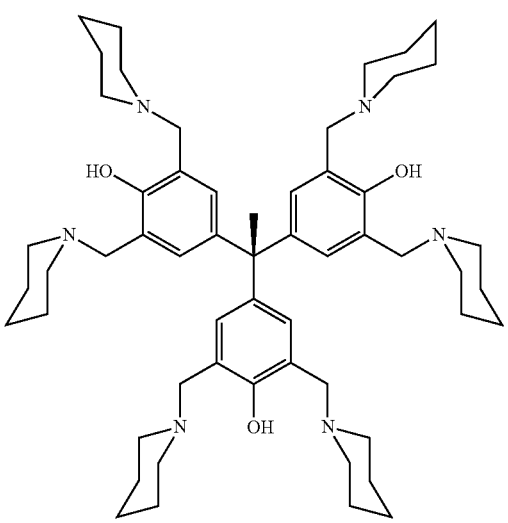

X

In another embodiment the structure of formula I is represented by the structure of formula XI:

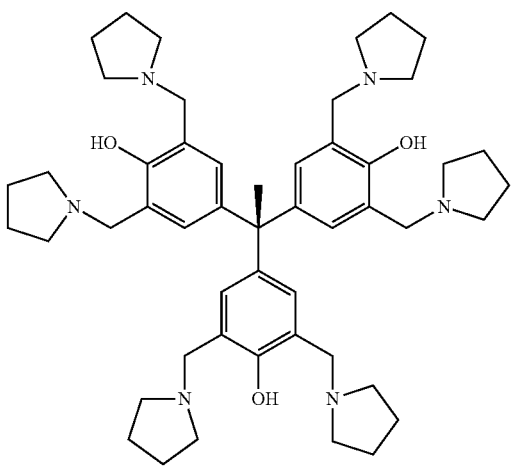

In another embodiment the structure of formula I is represented by the structure of formula XII:

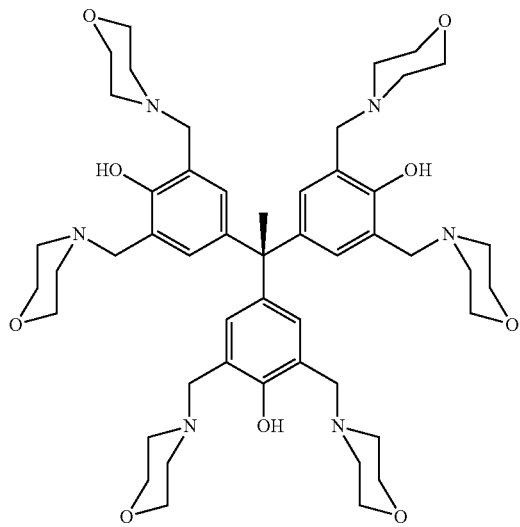

XII

In another embodiment the structure of formula I is represented by the structure of formula XIII:

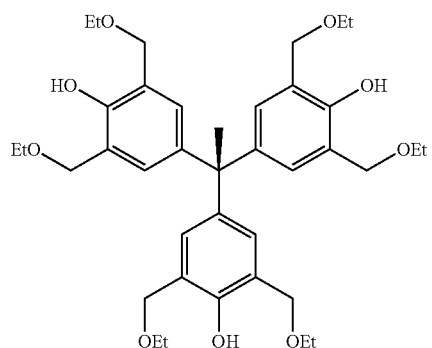

XIII

In another embodiment the structure of formula I is represented by the structure of formula XIV:

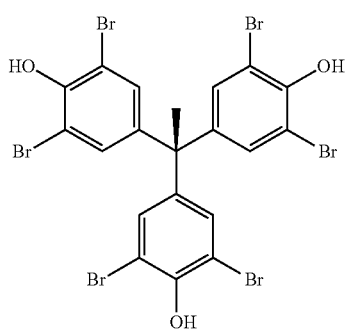

XIV

In another embodiment the structure of formula I is represented by the structure of formula XV:

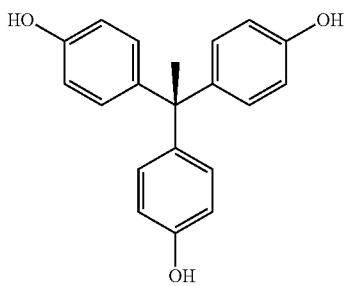

XV

In another embodiment the structure of formula I is represented by the structure of formula XVI:

XVI

In another embodiment, the invention makes use of pharmaceutical compositions comprising compounds as described herein for any method as described herein.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

Figure 1:
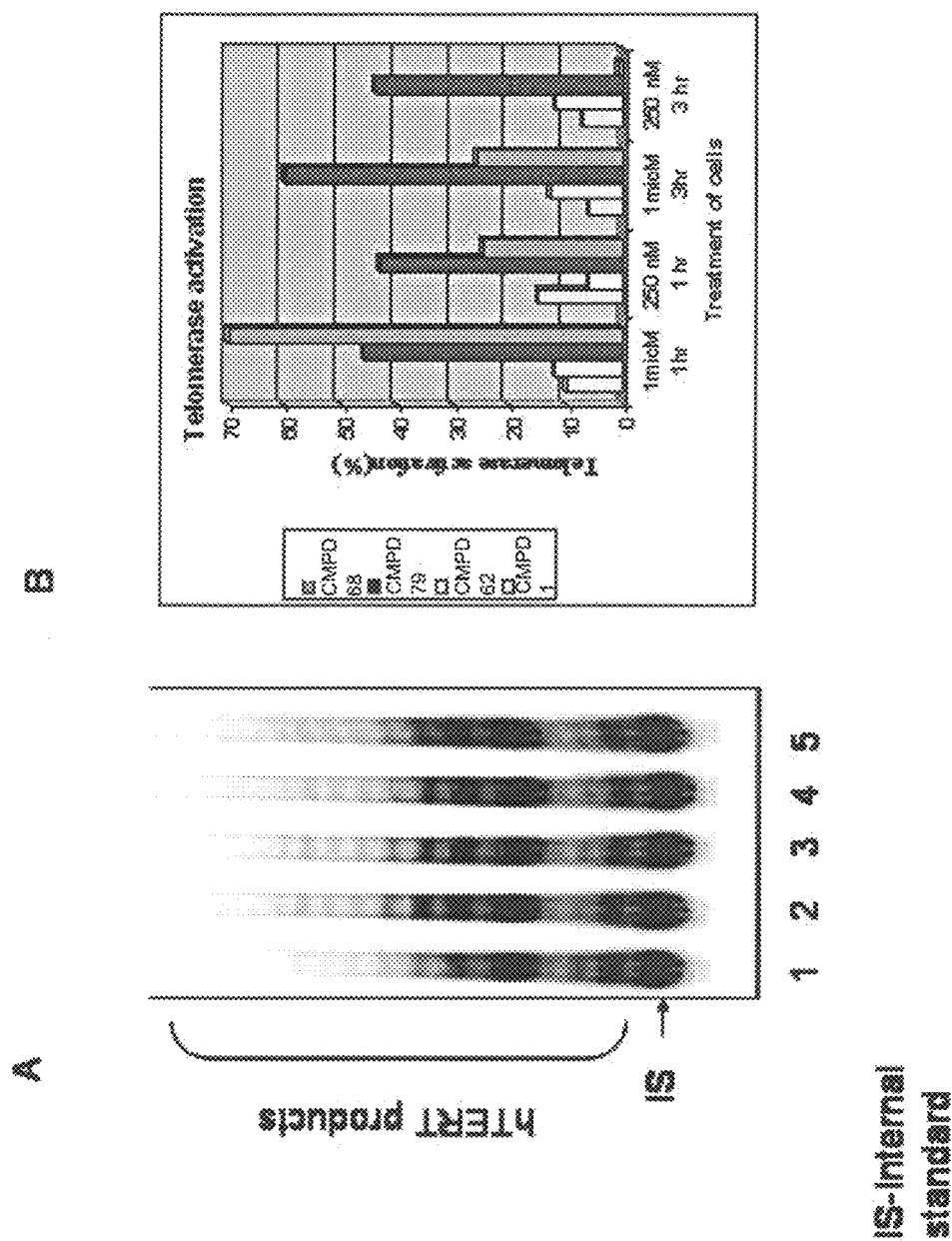
FIG. 1: Treatment of U-251 cell with compounds of the present invention and measurement of telomerase activity by TRAP assay. A. Telomerase activity in cells treated with Compound 68. B. Quantification of results and % telomerase activation.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention relates, in some embodiments, to the use of a novel class of tri-phenyl compounds and compositions comprising the same for the treatment of, inter alia, diseases or conditions capable of being affected by enhanced telomerase expression and/or telomerase activation.

The invention makes use of such compounds which stimulate and/or increase telomerase expression and/or activity in the cells and tissues of a subject, where the activity is decreased, missing, altered or normal. Such disorders include, inter alia, a) Alzheimer's disease; b) Parkinson's disease; c) Huntington's disease; d) nerve damage, motor neuron disease, multiple sclerosis (MS), peripheral and central nervous system injury including spinal injury and cerebral vascular incidents; e) stroke; f) diseases or conditions associated with aging, such as for example, aging of the skin such as dermal atrophy and thinning, elastolysis and skin wrinkling, sebaceous gland hyperplasia or hypoplasia, senile lentigo, pigmentation abnormalities, graying of hair and hair loss or thinning (baldness, alopecia), or chronic skin ulcers; g) degenerative joint disease; h) osteoporosis, osteoarthritis and other degenerative conditions of the skeletal system; i) sarcopenia and other degenerative conditions of the musculature; j) age- and stress-related diseases of the vascular system including atherosclerosis, calcification, thrombosis, and aneurysm; k) age-related macular degeneration; l) AIDS; m) age- and stress-related immune system impairment, including impairment of tissue turnover, which occur with natural aging, cancer, cancer therapy, acute or chronic infections, degenerative inflammatory diseases or with genetic disorders causing accelerated cell turnover, and related anemias and other degenerative conditions; n) healing of wounds, burns, abrasions or other acute or chronic conditions of epidermis; o) dyskeratosis congenita; p) luteal phase defect; q) premature ovarian failure (primary ovarian insufficiency or hypergonadotropic hypogonadism); and/or r) increasing telomerase expression and/or activity in memory T cells, thereby strengthening immune memory response and response to vaccines; s) increasing telomerase expression and/or activity in healthy tissue, thus elongating the lifespan of a subject while sustaining said subject in good health.

Compounds of the Invention:

In one embodiment, the methods of this invention comprise the use of tri-phenyl compounds represented by the structure of formula I:

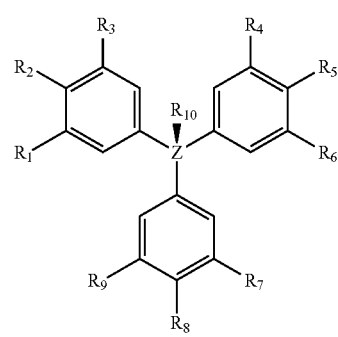

wherein

Z is carbon, nitrogen, phosphorous, arsenic, silicon or germanium;

$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula II:

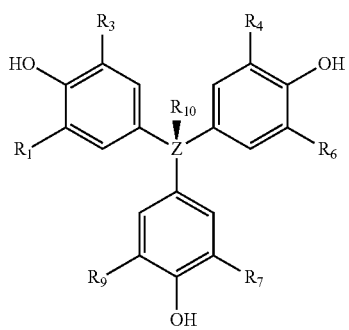

II wherein
Z is carbon, nitrogen, phosphorous, arsenic, silicon or germanium;

$R_1$, $R_3$, $R_4$, $R_6$, $R_7$ and $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment Z is carbon. In another embodiment $R_{10}$ is a methyl group. In another embodiment $R_1$, $R_3$, $R_4$, $R_6$, $R_7$, and $R_9$ are —$(CH_2)_n$-heterocycloalkyl group, wherein n is between 1-6. In another embodiment $R_1$, $R_3$, $R_4$, $R_6$, $R_7$, and $R_9$ are —$(CH_2)_n$-aminoalkyl group, wherein n is between 1-6. In another embodiment $R_1$, $R_3$, $R_4$, $R_6$, $R_7$, and $R_9$ are —$(CH_2)_n$-dialkylamino group, wherein n is between 1-6 In another embodiment $R_1$, $R_3$, $R_4$, $R_6$, $R_7$, and $R_9$ are —$(CH_2)_n$—$N(CH_3)_2$ group, wherein n is between 1-6. In another embodiment $R_1$, $R_3$, $R_4$, $R_6$, $R_7$, and $R_9$ are —$(CH_2)_n$—$N(Et)_2$ group, wherein n is between 1-6. In another embodiment $R_1$, $R_3$, $R_4$, $R_6$, $R_7$, and $R_9$ are —$(CH_2)_n$-aryl group, wherein n is between 1-6. In another embodiment $R_1$, $R_3$, $R_4$, $R_6$, $R_7$, and $R_9$ are —$(CH_2)_n$-heteroaryl group, wherein n is between 1-6. In another embodiment $R_1$, $R_3$, $R_4$, $R_6$, $R_7$, and $R_9$ are —$(CH_2)_n$-haloalkyl group, wherein n is between 1-6. In another embodiment $R_1$, $R_3$, $R_4$, $R_6$, $R_7$, and $R_9$ are —$(CH_2)_n$-alkoxy group, wherein n is between 1-6. In another embodiment $R_1$, $R_3$, $R_4$, $R_6$, $R_7$, and $R_9$ are —$(CH_2)_n$-ethoxy group, wherein n is between 1-6. In another embodiment $R_1$, $R_3$, $R_4$, $R_6$, $R_7$, and $R_9$ are —$(CH_2)_n$-cycloalkyl group, wherein n is between 1-6.

In one embodiment, the methods of this invention comprise the use of tri-phenyl compounds represented by the structure of formula III:

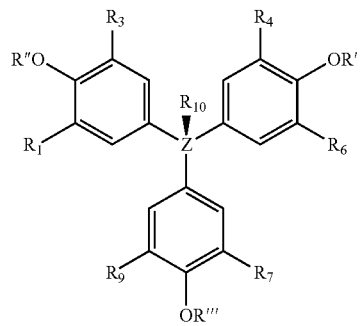

III wherein
Z is carbon, nitrogen, phosphorous, arsenic, silicon or germanium;

R', R" and R'" are independently the same or different comprising hydrogen, alkyl, haloalkyl, alkylamino, phenyl, benzyl, alkanyloyl, acetyl or benzoyl;

$R_1$, $R_3$, $R_4$, $R_6$, $R_7$ and $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula IV:

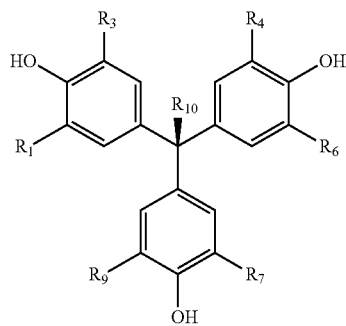

IV wherein $R_1$, $R_3$, $R_4$, $R_6$, $R_7$, $R_9$ and $R_{10}$ are as defined above; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula V:

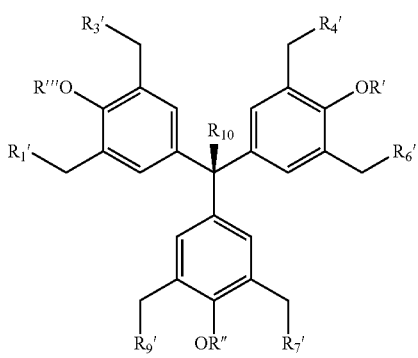

V wherein
R', R'', R''' are independently the same or different comprising hydrogen, alkyl, haloalkyl, phenyl, benzyl, alkanyloyl, acetyl or benzoyl;
$R_1'$, $R_3'$, $R_4'$, $R_6'$ $R_7'$, and $R_9'$ are the same or different comprising halogen, aryl, alkyl, cycloalkyl, heterocycloalkyl, alkoxy, amino, mono alkylamino, dialkylamino or arylamino group; and $R_7$ is as described above; or its isomer, pharmaceutically acceptable salt, pharmaceutical product, hydrate, N-oxide, crystal or any combination thereof, and compositions comprising the same.

In one embodiment, $R_1'$, $R_3'$, $R_4'$, $R_6'$ $R_7'$, and $R_9'$ are dialkylamino group. In another embodiment, $R_1'$, $R_3'$, $R_4'$, $R_6'$ $R_7'$, and $R_9'$ are dimethylamino group. In another embodiment, $R_1'$, $R_3'$, $R_4'$, $R_6'$ $R_7'$, and $R_9'$ are diethylamino group. In another embodiment, $R_1'$, $R_3'$, $R_4'$, $R_6'$ $R_7'$, and $R_9'$ are N-piperidine group. In another embodiment, $R_1'$, $R_3'$, $R_4'$, $R_6'$ $R_7'$, and $R_9'$ are N-pyrrolidine group. In another embodiment, $R_1'$, $R_3'$, $R_4'$, $R_6'$ $R_7'$, and $R_9'$ are N-piperazine group. In another embodiment, $R_1'$, $R_3'$, $R_4'$, $R_6'$ $R_7'$, and $R_9'$ are N-piperazine-4-methyl group. In another embodiment, $R_1'$, $R_3'$, $R_4'$, $R_6'$ $R_7'$, and $R_9'$ are N-morpholine group. In another embodiment, $R_1'$, $R_3'$, $R_4'$, $R_6'$ $R_7'$, and $R_9'$ are ethoxy group.

In one embodiment, the methods of this invention comprise the use of tri-phenyl compounds represented by the structure of formula VI:

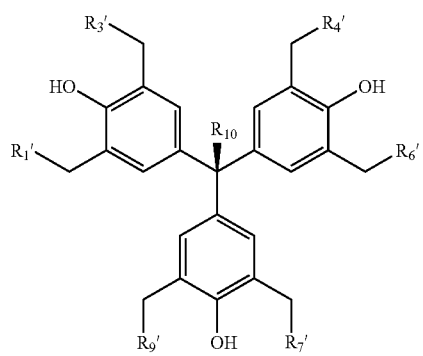

VI wherein $R_1'$, $R_3'$, $R_4'$, $R_6'$ $R_7'$, and $R_9'$ are the same or different comprising halogen, aryl, alkyl, cycloalkyl, heterocycloalkyl, alkoxy, amino, mono alkylamino, dialkylamino or arylamino group; and $R_{10}$ is as described above; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula VII:

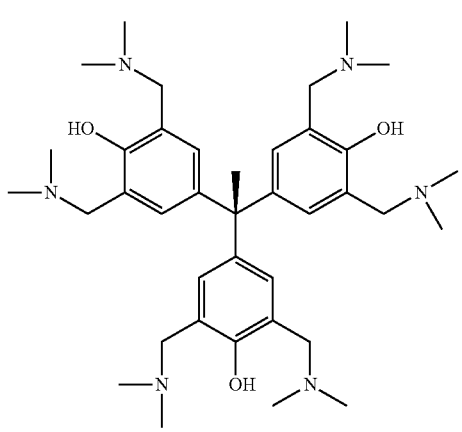

VII or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula VIII:

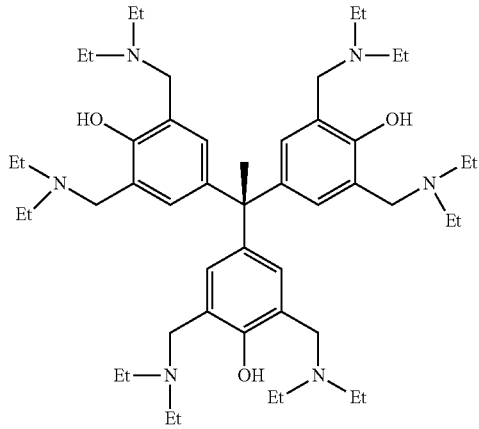

VIII or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula IX:

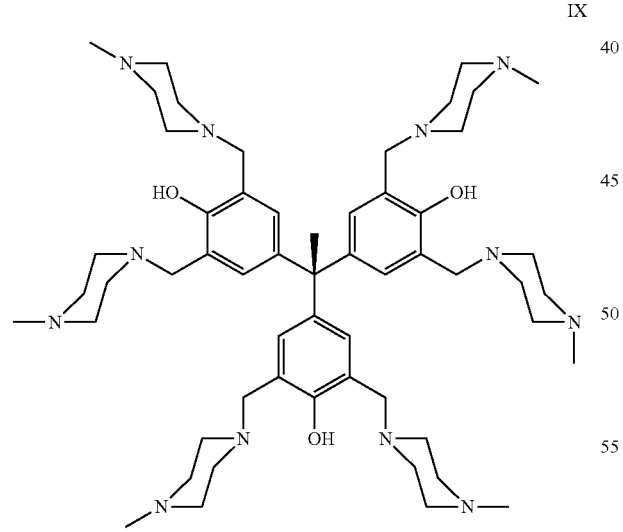

IX or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula X:

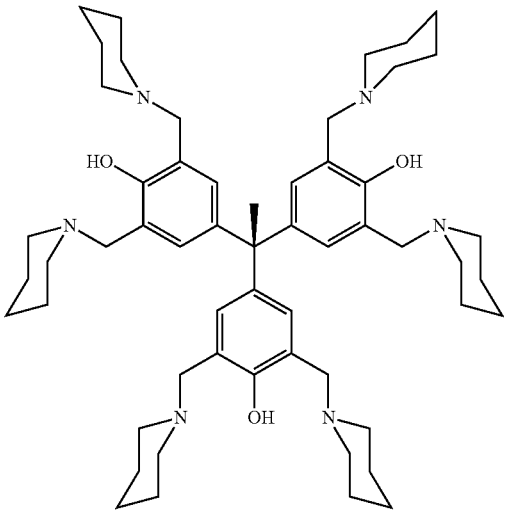

X or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XI:

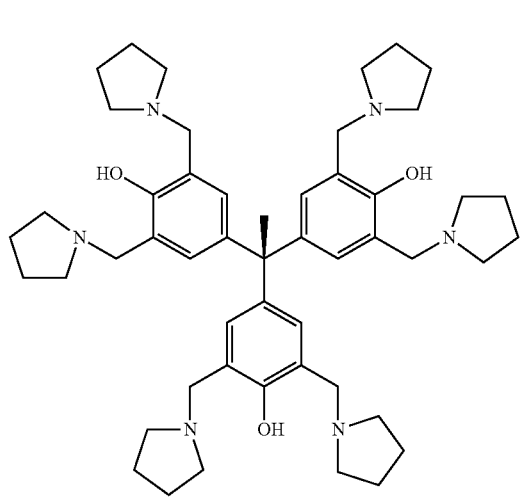

XI or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XII:

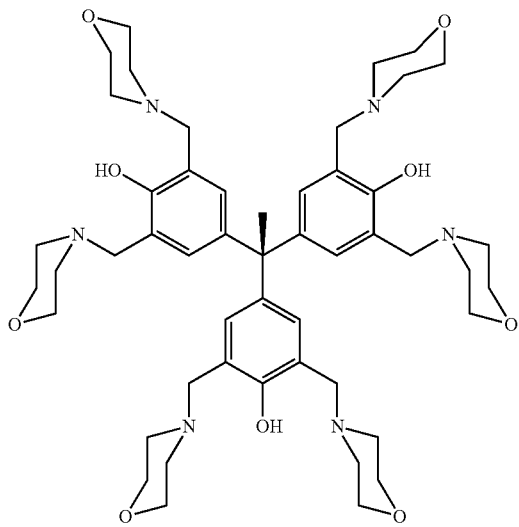

XII or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XIII:

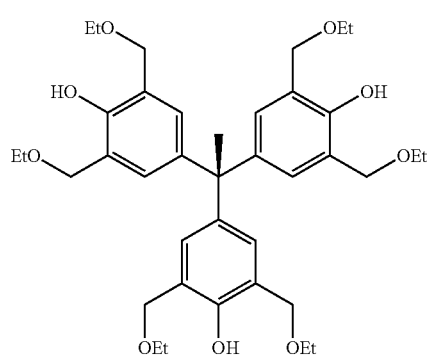

XIII or its isomer, pharmaceutically acceptable salt, pharmaceutical product, hydrate, N-oxide, crystal or any combination thereof, and compositions comprising the same.

In another embodiment the structure of formula I is represented by the structure of formula XIV:

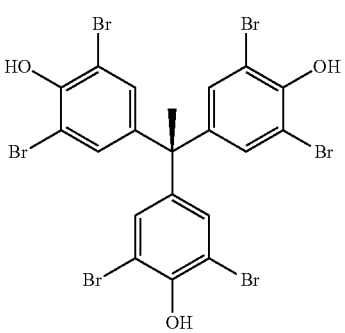

XIV or its isomer, pharmaceutically acceptable salt, pharmaceutical product, hydrate, N-oxide, crystal or any combination thereof, and compositions comprising the same.

In another embodiment the structure of formula I is represented by the structure of formula XV:

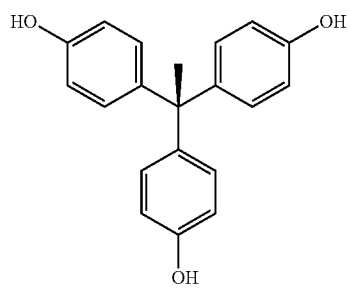

XV or its isomer, pharmaceutically acceptable salt, pharmaceutical product, hydrate, N-oxide, crystal or any combination thereof, and compositions comprising the same.

In another embodiment the structure of formula I is represented by the structure of formula XVI:

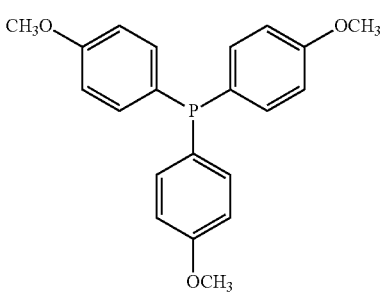

XVI or its isomer, pharmaceutically acceptable salt, pharmaceutical product, hydrate, N-oxide, crystal or any combination thereof, and compositions comprising the same.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-7 carbons. In another embodiment, the alkyl group has 2-6 carbons. In another embodiment, the alkyl group has 1-7 carbons. In another embodiment, the alkyl group has 2-8 carbons. In another embodiment, the alkyl group has 3-6 carbons. In another embodiment, the alkyl group has 3-7 carbons. In another embodiment, the alkyl group has 1-4 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy, carbonyl, amido, alkylamido, dialkylamido, nitro, cyano, amino, monoalkylamino, dialkylamino, carboxyl, thio and/or thioalkyl.

An "alkenyl" group refers, in one embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. In another embodiment the alkenyl group is ethenyl (CH═CH$_2$). Examples of alkenyl groups are ethenyl, propenyl, butenyl, cyclohexenyl, etc. The alkenyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An alkynyl" group refers, in one embodiment, to an unsaturated hydrocarbon, including straight chain, branched chain and cyclic groups having one or more triple bonds. The alkynyl group may have one triple bond, two triple bonds, triple double bonds, etc. In another embodiment, the alkynyl group has 2-12 carbons. In another embodiment, the alkynyl group has 2-6 carbons. In another embodiment, the alkenyl group has 2-4 carbons. In another embodiment the alkynyl group is ethynyl (—CH═CH$_2$). Examples of alkynyl groups are ethynyl, propynyl, butynyl, cyclohexynyl, etc. The alkynyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An "alkoxy" group refers, in another embodiment to an alkyl group as defined above, which is linked to oxygen. Examples of alkoxy groups are ethoxy, propoxy, tert-butoxy etc.

A "haloalkyl" group refers, in one embodiment, to an alkyl group as defined above, which is substituted by one or more halogen atoms, e.g. by F, Cl, Br or I.

An "aryl" group refers, in another embodiment, to an aromatic group having at least one carbocyclic aromatic group or heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the aryl group is between 4-12-membered ring(s). In another embodiment, the aryl group is between 6-18-membered ring(s). In another embodiment, the aryl group is between 4-8-membered ring(s). In another embodiment, the aryl group is a 6-membered ring. In another embodiment, the aryl group is a fused ring system comprising of between 2-3 rings. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "heteroaryl" group refers, in another embodiment, to an aromatic group having at least one heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the heteroaryl group is between 4-12-membered ring(s). In another embodiment, the heteroaryl group is between 6-18-membered ring(s). In another embodiment, the heteroaryl group is between 4-8-membered ring(s). In another embodiment, the heteroaryl group is a 6-membered ring. In another embodiment, the heteroaryl group is a fused ring system comprising of between 2-3 rings. Nonlimiting examples of heteroaryl rings are pyrrolyl, thienyl, thiazolyl, benzothienyl, naphthothienyl, purinyl, isothiazolyl, furyl, furazanyl, isobenznzofuranyl, pyranyl, chromenyl, xanthenyl, phenoxyxanthiinyl, indolyl, isoindolyl, indolizinyl, isoindolyzinyl, benzothienyl, oxazolyl, isoxazolyl, pyrazolyl, pyridyl, pyrazinyl, pyrimidinyl, pyridazinyl, and the like.

A "hydroxyl" group refers, in one embodiment, to an OH group. In some embodiments, when $R_1$, $R_2$ or $R_3$ of the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

An "amino" group refers to, in one embodiment, to a nitrogen atom attached by single bonds to hydrogen atoms, alkyl groups, alkenyl groups or aryl groups as described above, as described above, or a combination thereof. Nonlimiting examples of amino groups are $NH_2$, $N(Me)_2$, $N(Et)_2$, $N(Ph)_2$ and the like.

A "cycloalkyl" group refers, in one embodiment, to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$)cycloalkyl groups, such as cyclopropyl, cyclobutyl, cyclopentyl, cyclohexyl, and cycloheptyl, and saturated cyclic and bicyclic terpenes and ($C_3$-$C_7$)cycloalkenyl groups, such as cyclopropenyl, cyclobutenyl, cyclopentenyl, cyclohexenyl, and cycloheptenyl, and unsaturated cyclic and bicyclic terpenes. Preferably, the cycloalkyl group is a monocyclic ring or bicyclic to a ring structure comprising in addition to carbon atoms, sulfur, oxygen, nitrogen or any combination thereof, as part of the ring. In another embodiment the cycloalkyl is a 3-12-membered ring. In another embodiment the cycloalkyl is a 6-membered ring. In another embodiment the cycloalkyl is a 5-7-membered ring. In another embodiment the cycloalkyl is a 4-8-membered ring. In another embodiment, the cycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl.

A "heterocycloalkyl" group refers, in one embodiment, to a non-aromatic, monocyclic or polycyclic ring comprising carbon and in addition to carbon, sulfur, phosphorous, oxygen or nitrogen, as part of the ring. A heterocycloalkyl group can have one or more double bonds in the ring so long as the ring is not rendered aromatic by their presence. Examples of heterocycloalkyl groups include, but are not limited to, piperidine, piperazine, pyrane, morpholine. Preferably, the heterocycloalkyl group is a monocyclic ring or bicyclic to a ring structure comprising in addition to carbon atoms, sulfur, oxygen, nitrogen or any combination thereof, as part of the ring. In another embodiment the heterocycloalkyl is a 3-12-membered ring. In another embodiment the heterocycloalkyl is a 6-membered ring. In another embodiment the heterocycloalkyl is a 5-7-membered ring. In another embodiment the heterocycloalkyl is a 4-8-membered ring. In another embodiment, the heterocycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl. In another embodiment the heterocycloalkyl is a cyclic urea, imidazolinyl, imidazolidinyl, pyrrolinyl, pyrrolidinyl, oxazolinyl, isoxazolinyl, oxazolidinyl, oxazolidonyl, isoxazolidonyl, pyrazolinyl, pyrazolidinyl, piperidyl, piperazine, morpholinyl.

The terms "alkylalkoxy", "alkylhaloalkyl", "alkylaryl", "alkylcycloalkyl", "alkylheterocycloalkyl", "alkylheteroaryl" and "alkylamino" refer, in one embodiment, to an alkyl group, as defined above, linked to alkoxy, haloalkyl, aryl, cycloalkyl, heterocycloalkyl, heteroaryl or amino group, respectively. The alkoxy, haloalkyl, aryl, cycloalkyl, heterocycloalkyl, heteroaryl or amino groups are as defined hereinabove. Examples include, but are not limited to, $CH_2$—OEt, $CH_2$—N-piperidine, $CH_2$—N-piperazine, $CH_2$—N(Me)$_2$, etc.

In another embodiment, the fused heterocycloalkyl of formula I-IV with the main aromatic ring forms a phenylpyrrolidone group. In another embodiment, the fused aryl of formula I-IV, with the main aromatic ring forms a naphthalene group. In another embodiment, the fused heteroaryl of formula I-IV, with the main aromatic ring forms a quinoline or isoquinoline group.

In one embodiment, this invention provides for the use of a compound as herein described and/or, its analog, derivative, isomer, metabolite, pharmaceutically acceptable salt, pharmaceutical product, hydrate, N-oxide, prodrug, polymorph, impurity or crystal or combinations thereof.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the tri-phenyl compound. It is to be understood that the present invention encompasses any racemic, optically-active, polymorphic, or stereoisomeric form, or mixtures thereof, which form possesses properties useful in the treatment of telomerase expression and/or activity conditions described herein. In one embodiment, the tri-phenyl compounds are the pure (R)-isomers. In another embodiment, the tri-phenyl compounds are the pure (S)-isomers. In another embodiment, the tri-phenyl compounds are a mixture of the (R) and the (S) isomers. In another embodiment, the tri-phenyl compounds are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, in one embodiment, to form alkali metal salts and to form addition salts of free acids or free bases. Suitable pharmaceutically-acceptable acid addition salts of compounds of this invention may be prepared from an inorganic acid or from an organic acid. In one embodiment, examples of inorganic acids are hydrochloric, hydrobromic, hydroiodic, nitric, carbonic, sulfuric and phosphoric acid. In one embodiment, organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, oxalic, p-toluenesulphonic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. In one embodiment, suitable pharmaceutically-acceptable base addition salts of compounds of this invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds.

Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

The invention also includes use of N-oxides of the amino substituents of the compounds described herein.

This invention provides for the use of derivatives of the compounds as herein described. In one embodiment, "derivatives" includes but is not limited to ether derivatives, acid derivatives, amide derivatives, ester derivatives and the like. In another embodiment, this invention further includes use of hydrates of the compounds as described herein. In one embodiment, "hydrate" includes but is not limited to hemihydrate, monohydrate, dihydrate, trihydrate and the like.

This invention provides, in other embodiments, use of metabolites of the compounds as herein described. In one embodiment, "metabolite" means any substance produced from another substance by metabolism or a metabolic process.

This invention provides, in other embodiments, use of pharmaceutical products of the compounds as herein described. The term "pharmaceutical product" refers, in other embodiments, to a composition suitable for pharmaceutical use (pharmaceutical composition), for example, as described herein.

In some embodiments, the invention provides compositions comprising the compound of this invention or use of the compound of this invention, for increasing telomerase activity and/or expression in a cell or tissue; and/or treating a condition by increasing telomerase activity and/or expression in cells or tissue of a subject; and/or treating an acute or chronic condition of the epidermis; and/or elongation of a lifespan, and/or treating age- and stress-related diseases of the vascular system including atherosclerosis, calcification, thrombosis, hypertension or aneurysm; and/or treating age-related macular degeneration and/or age-related diseases of the skin; and/or treating age- and stress-related immune system impairment; and/or strengthening the immune response against infection-resistant organisms.

In some embodiments, the invention provides compositions comprising the compound of this invention and/or treating female infertility-related conditions including luteal phase defect or premature ovarian failure (primary ovarian insufficiency or hypergonadotropic hypogonadism); and/or diminished granulosa cell telomerase activity; and/or treating male infertility-related conditions including impaired sperm production or impaired sperm delivery; and/or as an adjunct to in vitro fertilization (IVF) techniques; and/or to enhance sperm quality and/or egg quality. For example, and in some embodiments, the compounds of this invention prolong blastocyst viability in ex vivo culture, which in turn enhances implantation efficiency. In some embodiments, the treatment of the population with the compounds as herein described renders them more receptive to other IVF therapeutics, or in some embodiments, allows for the evaluation of combination therapies, or new compounds.

In one embodiment, this invention provides methods of treatment using a compound of this invention, or composition comprising the same, as herein described. In some embodiments, the invention provides methods of use of a compound of this invention for the treatment of the indicated diseases, disorders or conditions, and includes use of compositions comprising the same.

In one embodiment, this invention provides methods of treating, suppressing, inhibiting, reducing the severity of, reducing the incidence of, reducing pathogenesis of or delaying onset of, inter alia, (a) Alzheimer's disease; (b) Parkinson's disease; (c) Huntington's disease; (d) stroke; e) nerve damage, motor neuron disease, multiple sclerosis (MS), peripheral and central nervous system injury including spinal injury and cerebral vascular incidents; (f) age-related diseases of the skin such as dermal atrophy and thinning, elastolysis and skin wrinkling, sebaceous gland hyperplasia or hypoplasia, senile lentigo, pigmentation abnormalities, graying of hair and hair loss or thinning (baldness, alopecia), or chronic skin ulcers; (g) degenerative joint disease; (h) osteoporosis, osteoarthritis and other degenerative conditions of the skeletal system; (i) age- and stress related diseases of the vascular system, including atherosclerosis, calcification, thrombosis, hypertension and aneurysm; (j) age-related macular degeneration; (k) AIDS; (l) age- and stress-related immune system impairment, including impairment of tissue turnover, which occurs with natural aging, cancer, cancer therapy, acute or chronic infections, degenerative inflammatory diseases or with genetic disorders causing accelerated cell turnover, and related anemias and other degenerative conditions; (m) healing of wounds, burns, abrasions or other acute or chronic conditions of epidermis; (n) dyskeratosis congenital; o) luteal phase defect; p) premature ovarian failure (primary ovarian insufficiency or hypergonadotropic hypogonadism); q) impaired sperm production or impaired sperm delivery; r) infection with infection-resistant organisms, via the administration of any compound as herein described and optionally other therapeutic agents, or compositions comprising the same.

In one embodiment, the terms "treating" or "treatment" includes preventive as well as disorder remittive treatment. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer, inter alia, to a genetic profile or familial relationship which is associated with a trend or statistical increase in incidence, severity, etc. of the indicated disease. In some embodiments, the term "predisposed to" is to be considered to refer, inter alia, to a lifestyle which is associated with increased risk of the indicated disease. In some embodiments, the term "predisposed to" is to be considered to refer, inter alia, to the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

The term "administering", in another embodiment, refers to bringing a subject in contact with a compound of the present invention. Administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of this invention make use of the described compound of this invention contacting or binding a telomerase enzyme in an amount effective to increase telomerase activity and/or expression and thereby mediating the described effects. In some embodiments, the methods of this invention may include the preliminary step of identifying a cell or tissue in which an increase telomerase activity and/or expression is desired. The cell may be in culture, i.e. in vitro or ex vivo, or within a subject or patient in vivo. In one embodiment, an increase in telomerase expression and/or activity in a cell or tissue includes, for example, enhancement of the replicative capacity and/or lifespan of the contacted cells.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compounds of this invention, together with a pharmaceutically acceptable carrier or diluent. A "therapeutically effective amount" as used herein refers to that amount which provides a therapeutic effect for a given condition and administration regimen.

In some embodiments, this invention provides compositions which may comprise at least one compound of this invention, in any form or embodiment as described herein. In some embodiments, the term "a" is to be understood to encompass a single or multiple of the indicated material. In some embodiments, the term "a" or "an" refers to at least one.

In some embodiments, any of the compositions of this invention will consist of a compound of this invention, in any form or embodiment as described herein. In some embodiments, of the compositions of this invention will consist essentially of a compound of this invention, in any form or embodiment as described herein.

In some embodiments, the term "comprise" refers to the inclusion of the indicated active agent, such as the compounds of this invention, as well as inclusion of other active agents, and pharmaceutically acceptable carriers, excipients, emollients, stabilizers, etc., as are known in the pharmaceutical industry. In some embodiments, any of the compositions of this invention will comprise a compound of formula I-XVI in any form or embodiment as described herein. In some embodiments, any of the compositions of this invention will consist of a compound of formula I-XVI, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" refers to a composition, whose only active ingredient with a comparable mode of action, or comparable molecular target is the indicated active ingredient, however, other active ingredients may be incorporated, with such secondary active ingredients acting on different targets, or in a palliative capacity. In some embodiments, the term "consisting essentially of" may refer to components which facilitate the release of the active ingredient. In some embodiments, the term "consisting" refers to a composition, which contains a compound as herein described as the only active ingredient and a pharmaceutically acceptable carrier or excipient.

In another embodiment, the invention provides a composition comprising a compound of this invention, as herein described, or its prodrug, analog, isomer, metabolite, derivative, pharmaceutically acceptable salt, pharmaceutical product, polymorph, crystal, impurity, N-oxide, ester, hydrate or any combination thereof and a suitable carrier or diluent.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions containing the compound of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound, sucrose as a sweetening agent methyl, and propylparabens as preservatives, a dye and flavoring, such as cherry or orange flavor. In addition, the active compounds may be incorporated into sustained-release, pulsed release, controlled release or postponed release preparations and formulations.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly (lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In one embodiment it will be desirable to deliver the compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363, all of which are fully incorporated by reference. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. It must be stable under the conditions of manufacture and storage and must be preserved against the contaminating action of microorganisms, such as bacteria and fungi.

In another embodiment, it will be preferable to include isotonic agents, for example, sugars or sodium chloride. In other embodiments, prolonged absorption of the injectable compositions will be desirable. Prolonged absorption of the injectable compositions can be brought about by the use of agents delaying absorption, for example, aluminum monostearate and gelatin, in the compositions.

Parenteral vehicles include in certain embodiments sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like In some embodiments, the compounds of this invention may be administered at various dosages to a subject, which in one embodiment, is a human subject. In one embodiment, the compounds of this invention are administered at a dosage of 0.1-200 mg per day. In one embodiment, the compound of this invention is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5-25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 1-30 mg, or in another embodiment, 30-50 mg, or in another embodiment, 30-75 mg, or in another embodiment, 100-2000 mg. In some embodiments, the compounds of this invention may be administered at different dosages, as a function of time, or disease/symptom/condition severity, or age, or other factors, as will be appreciated by one skilled in the art.

The compounds of this invention may be administered at various dosages. In one embodiment, the compounds of this invention are administered at a dosage of 1 mg. In another embodiment the compounds of this invention are administered at a dosage of 5 mg, or in another embodiment, 3 mg, or in another embodiment 10 mg, or in another embodiment 15 mg, or in another embodiment 20 mg, or in another embodiment 25 mg, or in another embodiment 30 mg, or in another embodiment 35 mg, or in another embodiment 40 mg, or in another embodiment 45 mg, or in another embodiment 50 mg, or in another embodiment 55 mg, or in another embodiment 60 mg, or in another embodiment 65 mg, or in another embodiment 70 mg, or in another embodiment 75 mg, or in another embodiment 80 mg, or in another embodiment 85 mg, or in another embodiment 90 mg, or in another embodiment 95 mg or in another embodiment 100 mg.

While the compounds of the invention can be administered as the sole active pharmaceutical agent, they can also be used in combination with one or more other compound, and/or in combination with other agents used in the treatment and/or prevention of the diseases, disorders and/or conditions, as will be understood by one skilled in the art. In another embodiment, the compounds of the present invention can be administered sequentially with one or more such agents to provide sustained therapeutic and prophylactic effects. In another embodiment, the compounds may be administered via different routes, at different times, or a combination thereof.

In addition, the compounds of the present invention can be used, either singly or in combination, in combination with other modalities for preventing or treating conditions, diseases or disorders. In some embodiments, such other treatment modalities may include without limitation, surgery, radiation, hormone supplementation, diet regulation, wound debridement, etc., as will be appropriate for the condition being treated. These can be performed sequentially (e.g., treatment with a compound of the invention following surgery or radiation) or in combination (e.g., in addition to a diet regimen).

The additional active agents may generally be employed in therapeutic amounts as indicated in the PHYSICIANS' DESK REFERENCE (PDR) 53rd Edition (1999), or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The pharmaceutical composition can comprise the compounds of this invention alone or can further include a pharmaceutically acceptable carrier and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulose materials, and mixtures thereof. The pharmaceutical preparation containing the compounds of this invention can be administered to a subject by, for example, subcutaneous implantation of a pellet; in a further embodiment, the pellet provides for controlled release of the compounds of this invention over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository. The pharmaceutical composition can also be a parenteral formulation; in one embodiment, the formulation comprises a liposome that includes a complex of a compound of this invention.

The pharmaceutical composition of the invention can be prepared by known dissolving, mixing, granulating, or tablet-forming processes. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant such as stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds of this invention or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, or pH buffering agents which enhance the effectiveness of the active ingredient.

For topical administration to body surfaces using, for example, creams, gels, drops, and the like, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Treatment of Conditions or Diseases Capable of being Affected by Telomerase Activation and/or Expression In some embodiments, this invention provides compounds, and pharmaceutical compositions comprising the same for the treatment of conditions and/or diseases capable of being affected by enhanced telomerase expression and/or activity. These compounds interact with the telomerase enzyme and stimulate and/or increase telomerase expression and/or activity in the tissues and cells of a subject. In some embodiment, such activity is decreased or absent, resulting in development of, or enhanced pathogenesis or symptoms associated with a disease, disorder or condition in the subject. Such disease, disorder or condition may comprise, inter alia, a) Alzheimer's disease; b) Parkinson's disease; c) Huntington's disease; d) stroke; e) nerve damage, motor neuron disease, multiple sclerosis (MS), peripheral and central nervous system injury including spinal injury and cerebral vascular incidents; f) age-related diseases of the skin such as dermal atrophy and thinning, elastolysis and skin wrinkling, sebaceous gland hyperplasia or hypoplasia, senile lentigo, pigmentation abnormalities, graying of hair and hair loss or thinning (baldness, alopecia), or chronic skin ulcers; g) degenerative joint disease; h) osteoporosis, osteoarthritis and other degenerative conditions of the skeletal system; i) age- and stress-related diseases of the vascular system including atherosclerosis, calcification, thrombosis, hypertension and aneurysm; j) age-related macular degeneration; k) AIDS; l) age- and stress-related immune system impairment, including impairment of tissue turnover, which occur with natural aging, cancer, cancer therapy, acute or chronic infections, degenerative inflammatory diseases or with genetic disorders causing accelerated cell turnover, and related anemias and other degenerative conditions; m) healing of wounds, burns, abrasions or other acute or chronic conditions of epidermis; n) dyskeratosis congenita; o) sarcopenia and/or other muscular disease or condition; p) luteal phase defect; q) premature ovarian failure (primary ovarian insufficiency or hypergonadotropic hypogonadism); r) impaired sperm production; s) impaired sperm delivery; and/or t) increasing telomerase expression and/or activity in memory T cells, thereby strengthening immune memory response and response to vaccines; and/or u) increasing telomerase expression and/or activity in healthy tissue, thus elongating the lifespan of a subject while sustaining said subject in good health and/or other clinical therapeutic and/or diagnostic areas, including any embodiment of what is encompassed by the term "treating" as described herein.

In some embodiments, the invention provides a method of increasing telomerase expression and/or activity in a cell or tissue, by contacting the cell or tissue with a composition comprising a compound of this invention. In one embodiment, the methods may include the step of identifying a cell or tissue in which an increase in telomerase expression and/or activity is desired.

Telomerase is typically detected at low levels in normal somatic cells. In skin, lymphocytic tissues, endometrial tissue, hair follicles and intestinal crypts, active mitotic cells and stem cells, telomerase expression and/or activity is expressed at low levels. Telomerase expression and/or activity is regulated at different molecular levels, including transcription, mRNA splicing, and via the maturation and modification of telomere reverse transcriptase (TERT) and telomere RNA component (TERC).

In one embodiment, the compounds and compositions of this invention activate telomerase, and methods as described herein are useful thereby.

The ability of a compound to increase telomerase expression and/or activity in a cell can be determined using the TRAP (Telomeric Repeat Amplification Protocol) assay, which is known in the art (e.g., Kim et al., U.S. Pat. No. 5,629,154; Harley et al., U.S. Pat. No. 5,891,639). The activity is typically compared to the activity similarly measured in a control assay of such cells (e.g., a telomerase activity 50% greater than observed in a solvent control). Cell lines suitable for use in the assay, may comprise normal human fibroblasts (Now) or normal human keratinocytes (NHK).

In some embodiments, the telomere length may serve as useful indicator for the telomerase expression and/or activity. In one embodiment, telomerase expression and/or activation is important in treating cancer, premature aging syndrome or segmental progeria, genetic anomalies and age-related diseases. The telomere length has distinct patterns of expression in specific disease progression, and is a function of its activation, thus measuring such length as a function of treatment has value, in some embodiments, in terms of the prognosis of different diseases.

In one embodiment, telomere length can be measured by Southern blot, hybridization protection assay, fluorescence in situ hybridization, flow cytometry, primed in situ, quantitative-polymerase chain reaction and single telomere length analysis, which are all techniques known in the art (Kah-Wai Lin and Ju Yan, *J. Cell. Mol. Med.*, 2005, Vol 9, No. 4, 977-989).

In some embodiments, this invention provides methods of treating a condition capable of being affected by telomerase expression and/or activation in a subject, the method comprising administering to a subject an effective amount of a compound of this invention, wherein the compound stimulates or enhances telomerase expression and/or activity in the cells or tissue of the subject.

In one embodiment, such conditions may comprise, for example, conditions associated with cellular senescence or with an increased rate of proliferation of a cell in the absence of telomerase, which leads to accelerated telomere repeat loss. The term "increased rate of proliferation" refers to higher rate of cell division compared to normal cells of that cell type, or compared to normal cells within other individuals of that cell type. The senescence of those groups of cells at an abnormally early age can eventually lead to disease.

In some embodiments, conditions which may be treated by increasing telomerase expression and/or activity may comprise use of the compounds as described herein in ex vivo cell therapy, as described further below, employing the appropriate associated cell types. In one embodiment, the condition is Alzheimer's disease, Parkinson's disease, Huntington's disease, stroke, nerve damage, motor neuron disease, multiple sclerosis (MS), or peripheral and central nervous system injury including spinal injury and cerebral vascular incidents; wherein the cells that may be employed are cells of the central nervous system, including neurons and/or glial cells, e.g., astrocytes, endothelial cells and/or fibroblasts. In another embodiment, the condition is glutamate-induced apoptosis in the cerebellum.

In another embodiment, the condition is an age-related disease of the skin, such as dermal atrophy and thinning, elastolysis and skin wrinkling, sebaceous gland hyperplasia or hypoplasia, senile lentigo and/or other pigmentation abnormalities, graying of hair and hair loss or thinning (baldness, alopecia), or chronic skin ulcers; wherein the cells that may be employed are fibroblasts, sebaceous gland cells, melanocytes, keratinocytes, Langerhan's cells, microvascular endothelial cells and/or hair follicle cells.

In another embodiment, the condition is a degenerative joint disease; wherein the cells that may be employed are cells of the articular cartilage, such as chondrocytes and lacunal and/or synovial fibroblasts.

In another embodiment, the condition is osteoporosis, osteoarthritis and/or other degenerative conditions of the skeletal system; wherein the cells that may be employed are cells of the skeletal system, such as osteoblasts, bone marrow stromal or mesenchymal cells and/or osteoprogenitor cells.

In another embodiment, the condition is sarcopenia and/or other degenerative conditions of the musculature; wherein the cells that may be employed are cells are muscle cells, or progenitor cells thereof or mesenchymal cells.

In another embodiment, the condition is an age- and/or stress-related disease of the vascular system including atherosclerosis, calcification, thrombosis, hypertension and aneurysms; wherein the cells that may be employed are cells of the heart and vascular system, including endothelial cells, smooth muscle cells, and/or adventitial fibroblasts.

In another embodiment, the condition is age-related macular degeneration; wherein the cells that may be employed are cells of the eye, such as pigmented epithelium and/or vascular endothelial cells.

In another embodiment, the condition is acquired immune deficiency or AIDS; wherein the cells that may be employed are T lymphocytes, such as CD4+ or CD8+ T cells. In another embodiment, the condition is congenital immune deficiency.

In another embodiment, the condition is graft-versus-host disease (GVHD). In another embodiment, the condition is graft-versus leukemia disease (GVL).

In another embodiment, the condition is age- and/or stress-related immune system impairment, including impairment of tissue turnover, which occurs with natural aging, cancer, cancer therapy, acute or chronic infections, degenerative inflammatory diseases or with genetic disorders causing accelerated cell turnover, and related anemias and other degenerative conditions, wherein the cells that may be employed are other cells of the immune system, including cells in the lymphoid, myeloid, and erythroid lineages, such as B and T lymphocytes, monocytes, circulating and specialized tissue macrophages, neutrophils, eosinophils, basophils, NK cells, and their respective progenitors.

In some embodiments, the methods and/or compositions of this invention find application in improving immune function in disease or in health. In some embodiments, the methods and/or compositions of this invention find application in enhancing T cell activity, for example cytotoxic T lymphocyte activity or responsiveness, or rescue from anergy, which may find application in treating multiple diseases, for example in infection or neoplasia. In some embodiments, such methods and/or compositions are particularly useful in treating pathogens highly resistant to conventional therapy, particularly virulent organisms, or organisms for which no other therapies are available, for example, multi-drug-resistant organisms.

In another embodiment, the condition is female fertility-related, including luteal phase defect, wherein there is a disruption in the normal female menstrual cycle and the body does not produce enough progesterone, resulting in a delay in the development of the lining of uterus (endometrium), or premature ovarian failure (primary ovarian insufficiency or hypergonadotropic hypogonadism), wherein there is a loss of normal functioning of the ovaries in a woman younger than age 40.

In another embodiment, the condition is male fertility-related, including impaired sperm production or impaired sperm delivery.

In another embodiment, cell types in which an increase in telomerase expression and/or activity can be therapeutically beneficial include, but are not limited to, cells of the liver, endocrine and exocrine glands, smooth musculature, or skeletal musculature.

In one embodiment, AIDS disease is believed to be caused by the early senescence of CD8+ cells. The aging of such cells is attributed not simply to an abnormal amount of loss of telomere sequences per cell doubling, but, in addition, to the increased replicative rate of the cells, such that telomere attrition is greater than normal for that group of cells. The invention thus provides methods of treating an HIV infected subject, and more particularly of reducing early senescence of HIV-restricted CD8+ cells in an HIV infected subject, comprising administering to said subject a compound of this invention or a composition comprising the same.

In one embodiment an increase in telomerase expression and/or activity can benefit non-dividing cells as well as proliferating cells, e.g. in conditions associated with increased susceptibility to cell death due to stress, such as ischemia in heart failure or in stroke (Schneider, *J. Mol. Cell. Cardiol* 34(7):717-24; Mattson, *Exp Gerontol.* 35(4):489-502). This invention provides methods of reducing stress- or DNA damage-induced cell death in a subject, such as a subject experiencing ischemic conditions in tissue due to heart failure or stroke, by increasing telomerase expression and/or activity in cells of the subject, comprising administering to said subject a composition comprising a compound of this invention.

In one embodiment, this invention provides methods for extending the lifespan of a subject and whose life can be extended by extending the ability of those cells to continue replication or resist stress-induced cell death. One example of such a group of cells is lymphocytes present in Down's Syndrome patients. The invention thus provides a method of enhancing replicative capacity and/or lifespan of lymphocytes present in a Down's Syndrome patient, by increasing telomerase expression and/or activity in said cells of the patient, comprising administering to said subject a composition comprising a compound of this invention. The compositions may also be used to improve resistance to stress-induced cell death occurring during normal aging.

In one embodiment, this invention provides methods of increasing telomerase expression and/or activity and thereby promote healing of wounds, burns, abrasions or other acute or chronic conditions of the skin, and in some embodiment, in particular in the epidermis. The invention thus provides a method of treating an acute or chronic condition of the skin, by administering to said subject a compound as herein described and/or a composition comprising the same. In one embodiment, the composition is topically administered to the affected area.

In another embodiment, acute or chronic skin conditions treated via the methods of this invention may comprise lesions suffered in trauma, burns, abrasions, surgical incisions, donor graft sites, and/or lesions caused by infectious agents.

In another embodiment, the acute or chronic conditions of the skin may comprise chronic venous ulcer, diabetic ulcer, compression ulcer, pressure sores, and ulcers or sores of a mucosal surface.

In another embodiment, the acute or chronic condition of the skin may comprise surface lesions caused by a persistent inflammatory condition or infection, or by a genetic defect (such as Haloid formation and coagulation abnormalities).

In one embodiment, the methods of healing of wounds, burns, abrasions or other acute or chronic conditions of the skin comprises administering a composition comprising a compound as herein described to stimulate or enhance cell proliferation or migration at the treatment site, increase in density of epithelial cells at the site as a result of the applied therapy and thereby closure of a wound if present, or restoration of normal physiological function.

In one embodiment, this invention contemplates manipulation of the skin and repair of any imperfection of the skin surface for other purposes, such as cosmetic enhancement.

In another embodiment, compounds and compositions as herein described may be utilized for protecting skin from UV radiation, or palliative treatment of damage thereby.

In another embodiment, the methods and compositions of the invention can be used in treating hair conditions, in preserving hair color, hair shine or quality. In some embodiments, methods and compositions of the invention can be used in treating hair loss, or as adjunctive therapy with hair replacement and hair loss treatment protocols.

In another embodiment, the methods and compositions of the invention can be used in agricultural applications. In one embodiment, compounds and compositions as herein described may be utilized to increase plant crop yields, wherein, in one embodiment, fruit yield is increased and in another embodiment, fruit size is increased. In another embodiment, the compounds and compositions as herein described may be utilized to increase milk production in dairy cattle, while in another embodiment, egg size may be increased. In another embodiment, meat production may be increased in domestic animals raised for meat, including chickens, cows and pigs. In yet another embodiment, the compounds and compositions as herein described may be utilized in the horse racing industry, to increase reproductive ability of both stallions and mares, and to increase muscle strength and stamina for greater racing speeds.

In one embodiment, the methods and compositions of the invention can be used to enhance replicative capacity and/or extend lifespan of cells in culture, e.g., in ex vivo cell therapy or in monoclonal antibody production, by increasing telomerase expression and/or activity in the cells. Increasing telomerase expression and/or activity increases the replicative capacity of such cells by slowing telomere repeat loss and/or improving resistance to stress-induced cell death during cell proliferation.

In one embodiment, the methods and compositions of the invention may be useful in allogeneic cell therapy, which may include, in one embodiment, stem cell transplantation, donor cell transplantation or cancer immunotherapy. In another embodiment, the methods and compositions of the invention may be useful in the activation and/or mobilization of stem cells. For example, and in some embodiments, the methods and compositions of the invention may be useful in enhancing survival of stem cells in ex vivo culture. In some embodiments, the methods and compositions of the invention may prolong culture time, thereby supporting expansion of the cell population, which in turn enhances transplantation efficiency, while in other embodiments, the methods and compositions of the invention may increase cell viability and/or may increase lifespan of the cells at the stem cell stage, prior to cell differentiation. In some embodiments, the treatment of the population with the compounds as herein described renders them more receptive to other stem cell manipulations, for example transformation or transduction.

In one embodiment, the stem cells may be embryonic stem cells, while in another embodiment; the stem cells may be adult stem cells. In one embodiment, the methods and compositions of the invention may be useful for culturing stem cells in vitro. In another embodiment, the methods and compositions of the invention may be useful in culturing non-stem cells in vitro. In one embodiment, the methods and compositions of the invention may be useful for culturing, inter alia, pancreatic beta cells in vitro. In another embodiment, the methods and compositions of the invention may be useful for tissue engineering. In another embodiment, the stem cells may be cancer stem cells. In one embodiment, the methods and compositions of the invention may be useful in treating aplastic anemia.

In some embodiments, the methods and compositions of this invention are useful as an adjunctive therapy in treating cancer, in combination with surgical, radiation, chemotherapeutic and immunotherapeutic methods/compounds, and in enhancing responsiveness to other cancer therapeutics. In some embodiments, the compounds of this invention suppress cancer latency, i.e. maintain neoplastic cells in an active state whereby additional compounds which are toxic to cancer cells are more effective. In some embodiments, the methods and compositions of this invention when comprising adjunctive therapy for cancer increase the likelihood of survival of a subject with cancer. In some embodiments, the methods and compositions of this invention may prevent damage to developing embryos caused by drug treatment, which may, in one embodiment, may be anti-cancer drug treatment. In some embodiments, the methods and compositions of this invention are useful in the development of cancer diagnostics. For example, and in some embodiments, the compounds of this invention expand populations of hard to detect cancer cells, aiding in their detection, thereby being a means/method of cancer diagnostics. In some embodiments, staging of the cancer may be a reflection of the responsiveness to the compounds as herein described.

In some embodiments, the methods and compositions of this invention are useful in the development of novel treatment regimens. For example, and in some embodiments, the compounds of this invention expand populations of difficult to detect or difficult to treat cancer cell populations, which in turn allows for the design of anticancer compounds more suitable for the treatment of the particular cancerous cell population. In some embodiments, the treatment of the population with the compounds as herein described renders them more susceptible to other anticancer therapeutics, or in some embodiments, allows for the evaluation of combination therapies, or new compounds.

In some embodiments, the methods and compositions of this invention are useful in cancer stem cell expansion, which in turn is useful in the development of therapies and treatments for cancers comprising such cells. In some embodiments, the methods and compositions of this invention useful in cancer stem cell expansion, disease staging and diagnosis of the cancer.

In one embodiment, the methods and compositions of the invention may be useful in facilitating transdifferentiation of cells, while in another embodiment, they may be useful in cell cloning and/or in transduction or transformation. In another embodiment, the methods and compositions of the invention may be useful in enhancing plasmid or naked DNA uptake, liposome uptake, etc., in cells, resulting in some embodiments, in enhanced nucleic acid transformation efficiency.

In one embodiment, this invention provides methods for increasing the replicative capacity and/or lifespan of the cells by ex vivo applications, wherein a compound of this invention is added to explant cells obtained from a subject, thereby increasing the replicative capacity and/or lifespan of the cells.

The explant cells may include, for example, stem cells, such as bone marrow stem cells (U.S. Pat. No. 6,007,989), bone marrow stromal cells (Simonsen et al., Nat Biotechnol 20(6):592-6, 2002), or adrenocortical cells (Thomas et al., Nat Biotechnol 18(1):39-42, 2000). Disease conditions of this invention may also be subject to ex vivo cell-based therapy. Examples include the use of muscle satellite cells for treatment of muscular dystrophy, osteoblasts to treat osteoporosis, retinal pigmented epithelial cells for age-related macular-degeneration, chondrocytes for osteoarthritis, etc.

In one embodiment, this invention provides methods for treating dyskeratosis congenita, comprising administering a compound a composition comprising a compound of this invention.

Dyskeratosis congenita (DKC), also known as Zinsser-Engman-Cole syndrome, is a rare, progressive bone marrow failure syndrome characterized by the triad of reticulated skin hyperpigmentation, nail dystrophy, and oral leukoplakia. The gene mutated in X-linked DKC (DKC1) encodes a highly conserved nucleolar protein called dyskerin. Evidence exists for telomerase dysfunction, ribosome deficiency, and protein synthesis dysfunction in this disorder. Early mortality is often associated with bone marrow failure, infections, fatal pulmonary complications, or malignancy.

Patients with DKC have reduced telomerase expression and/or activation and abnormally short tracts of telomeric DNA compared with normal controls. Because telomeres function to maintain chromosomal stability, telomerase has a critical role in preventing cellular senescence and cancer progression. Both DKC and a subset of aplastic anemia are due to a defect in telomerase.

In one embodiment, the invention provides a method of stem cell proliferation, wherein a stem cell population is treated with a compound of this invention and thereby enhances the replicative capacity and/or lifespan of the cell population.

In some embodiments, the invention provides for the use of compounds and/or compositions as herein described as therapeutic agents to forestall and reverse cellular senescence, including but not limited to conditions associated with cellular senescence. In some embodiments, the compounds and/or compositions as herein described may be used in cell or organ culture media, to expand primary cell cultures for purposes of, inter alia, diagnosis, analysis or vaccine production, or to maintain the viability of an organ/cells prior to transplantation (during ischemic time, the time between the interruption and reestablishment of blood supply). In some embodiments, the invention provides for the use of compounds and/or compositions as herein described are useful in prolonging survival of cells or tissue for transplantation, and/or in some embodiments, promote greater incorporation of such grafts. In some embodiments, such properties find utility in particular in applications such as islet or marrow cell transplantation, stem cell transplantation or tissue engineering.

In some embodiments, the invention provides for the use of compounds and/or compositions as herein described as stimulants of (a) cells with replicative capacity in the central nervous system, including astrocytes, endothelial cells, and fibroblasts which play a role in such age-related diseases as Alzheimer's disease, Parkinson's disease, Huntington's disease, and stroke, or in repairing nerve damage, motor neuron disease, peripheral and central nervous system injury including spinal injury and cerebral vascular incidents (CVI) such as stroke, or in diseases such as multiple sclerosis (MS); (b) cells with finite replicative capacity in the integument, including fibroblasts, sebaceous gland cells, melanocytes, keratinocytes, Langerhans cells, and hair follicle cells which may play a role in age-related diseases of the integument such as dermal atrophy, elastolysis and skin wrinkling, sebaceous gland hyperplasia, senile lentigo, graying of hair and hair loss (baldness, alopecia), chronic skin ulcers, keratosis and age-related impairment of wound healing; (c) cells with finite replicative capacity in the articular cartilage, such as chondrocytes and lacunal and synovial fibroblasts which play a role in degenerative joint disease; (d) cells with finite replicative capacity in the bone, such as osteoblasts and osteoprogenitor cells which play a role in osteoporosis; (e) cells with finite replicative capacity in the immune system such as B and T lymphocytes, monocytes, neutrophils, eosinophils, basophils, NK cells and their respective progenitors, which may play a role in age-related immune system impairment; (f) cells with finite replicative capacity in the vascular system including endothelial cells, smooth muscle cells, and adventitial fibroblasts which may play a role in age-related diseases of the vascular system including atherosclerosis, calcification, thrombosis, hypertension and aneurysms; (g) cells with finite replicative capacity in body organs including, but not limited to liver, lung and pancreas (islet cells), which may play a role in liver disease (cirrhosis), lung disease or diabetes; (h) cells with finite replicative capacity in the reproductive system, including ovarian follicle cells and corpus luteum cells; (i) cells with finite replicative capacity in the ear, including inner and outer ciliated auditory cells of the organ of Corti; and (j) cells with a finite replicative capacity in the eye such as pigmented epithelium and vascular endothelial cells which may play an important role in age-related macular degeneration.

The following examples are presented in order to more fully illustrate the preferred embodiments of the invention. They should in no way be construed, however, as limiting the broad scope of the invention.

EXAMPLES

Example 1

Synthesis of Compound 77

1,1,1-tris(4-hydroxyphenyl)ethane (4 g, 13 mM), formaldehyde (3.6 g, 120 mM) and a 40% solution of dimethylamine in water (15 ml) were added to a solution of 50 ml water and 60 ml EtOH. The solution was refluxed for 2.5 hours. Partial evaporation of the solvent precipitated a white solid, which was filtered, washed with water and dried to give 7.85 g white solid of compound 77, 93% yield, mp.=169°.
NMR CDCl$_3$ δ 6.64 (6H, s, ArH), 3.40 (12H, s, CH$_2$), 2.22 (36H, s, N—CH$_3$), 2.06 (3H, s, C—CH$_3$).

Example 2

Synthesis of Compound 84

Compound 84 was synthesized by a process comparable to that described in Example 1.
NMR CDCl$_3$ δ 6.71 (6H, s, ArH), 3.58 (12H, s, CH$_2$), 2.54 (24H, q, J=7.0 Hz), 1.04 (24H, t, J=7.0 Hz).

Example 3

Synthesis of Compound 78

1,1,1-tris(4-hydroxyphenyl)ethane (1.53 gr, 5 mM), formaldehyde (1.35 gr, 45 mM) and 1-methyl piperazine (2.5 ml, 50 mM) in 20 ml water and 25 ml EtOH were refluxed for 3 hours. Evaporation provided a solid that by TLC and NMR contained 2 products, which was not the starting material. Formaldehyde (0.75 gr, 25 mM) and 1-methyl piperazine (1.5 ml, 30 mM) were added to 5 ml water and 10 ml EtOH and the reaction was refluxed for 4 hours. Evaporation and workup gave 3.3 gr light yellow-white solid, 67% yield, mp. 63°. Soluble in ethanol, and very good solubility in water.
NMR CDCl$_3$ δ 6.67 (6H, s, ArH), 3.53 (12H, s, CH$_2$), 2.44 (48H, br.m, ring piperazine), 2.26 (18H, s, N—CH$_3$), 2.00 (3H, s, C—CH$_3$).

Example 4

Synthesis of Compound 83

Compound 83 was synthesized by a process comparable to that described in Example 1. A white solid was obtained. mp.=178°.
NMR CDCl$_3$ δ 6.68 (6H, s, ArH), 3.55 (12H, s, CH$_2$), 2.51 (24H, br.t, N—CH$_2$ ring), 2.03 (3H, s, C—CH$_3$), 1.55 (24H, br.t, N—CH$_2$ ring), 1.42 (12H, br.s).

Example 5

Synthesis of Compound 81

Compound 81 was synthesized by a process comparable to that described in Example 1. A white solid was obtained. m.p.=135°.
NMR CDCl$_3$ δ 6.68 (6H, s, ArH), 3.61 (12H, s, CH$_2$), 2.51 (24H, br.t, N—CH$_2$ ring), 2.03 (3H, s, C—CH$_3$), 1.76 (24H, br.t, N—CH$_2$ ring).

Example 6

Synthesis of Compound 82

Compound 82 was synthesized by a process comparable to that described in Example 1. A white solid was obtained. mp.=212°.
NMR CDCl$_3$ δ 6.68 (6H, s, ArH), 3.69 (24H, t, J=4.5 Hz, N—CH$_2$ ring), 3.52 (12H, s, CH$_2$), 2.45 (24H, br.t, O—CH$_2$ ring), 2.03 (3H, s, C—CH$_3$).

Example 7

Synthesis of Compound 79

Step 1: Compound 77 (2.98 g, 4.6 mM), prepared by a process as described in Example 1, was added to 20 ml acetic anhydride, and heated to 100° for 4 hours. The mixture was cooled and water was added. The mixture was stirred overnight at room temperature, and then extracted with $CH_2Cl_2$. The solvent was evaporated to give a nona-acetate derivative as yellow oil and was further purified by chromatography (silica gel; 1% $MeOH/CH_2Cl_2$) to give 3.2 g of viscous yellow oil, 80% yield.

Step 2: A KOH (4 g) solution in water was added to a solution of the nona-acetate of step 1 (2.5 g) in 20 ml EtOH. The mixture was stirred for 20 hours at room temperature. The mixture was acidified with HCl, and extracted with $CH_2Cl_2$. The solvent was evaporated and gave 2.2 g of a yellow oil that and was further purified by column chromatography (silica gel; 2% $MeOH/CH_2Cl_2$) and recrystallyzed from toluene-hexane to give 1 gr of compound 79, 53% yield, white solid, mp 78°. TLC-Rf=0.55 in 5% MeOH/ $CH_2Cl_2$.

NMR $CDCl_3$ δ 7.93 (3H, s, OH), 6.79 (6H, s, Ar—H), 4.54 (12H, s, Ar—$CH_2$), 3.55 (12H, q, J=7.0 Hz, $CH_2$), 2.05 (3H, s, C—$CH_3$), 1.22 (18H, t, J=7.0 Hz, $CH_3$).

Example 8

Synthesis of
1,1,1-tris(4-hydroxy-3,5-dibromo-phenyl)-ethane
(Compound 68)

Step 1: A solution of NaOH (1 g, 25 mM) in 10 ml water and dimethyl sulphate (5.1 gr, 40 mM) (1:8 molar ratio) was added during 1 hour and simultaneously in portions to a solution of 1,1,1-tris(4-hydroxyphenyl)-ethane (1.53 g, 5 mM) in 20 ml ethanol and 10 ml water. The solution was then refluxed for 1 hour, and stirred 70 hours at RT. The white precipitate was filtered, washed with water and dried to give 1.74 g of 1,1,1-tris (4-methoxyphenyl)-ethane. Recrystallization twice from 50 ml ethanol gave 1.15 gr white crystals, 66% yield, and m.p. 160°. TLC Rf=0.85 in $CH_2Cl_2$.

NMR $CDCl_3$ δ 6.99, 6.79 (12H, $AB_q$, $J_{AB}$=8.8 Hz), 3.78 (9H, s, $OCH_3$), 2.11 (3H, s, $CH_3$).

Step 2: To a solution of 1,1,1-tris (4-methoxyphenyl)-ethane (0.49 gr, 1.4 mM), from step 1, in 22 ml 1,2-dichloroethane, a solution of bromine (1.65 gr, 10.2) (7.3:1 ratio) in 5 ml 1,2-dichloroethane was added in portions. The solution was stirred at RT overnight and heated for 3 hours to 70°, and worked up (sodium thiosulphate) to give 1.0 gr crude product. TLC shows no starting material, but NMR showed mixtures, indicating that the bromination was not complete (m at 6.90 ppm, and 4 methoxy). The solid was brominated again with 1 gr bromine and refluxed 18 hours. The mixture was worked up as above and triturated with hot ethanol to give 0.27 gr white solid, 23% yield, mp=160°. TLC Rf=0.95 in $CH_2Cl_2$.

NMR $CDCl_3$ δ 7.16 (6H, s, ArH), 3.92, 3.91 (6:4 ratio) (9H, 2s, $OCH_3$), 2.04, 2.03 (4:6 ratio) (3H, s, $CH_3$).

Example 9

Synthesis of
1,1,1-tris(4-hydroxy-3,5-diiodo-phenyl)-ethane

To 1,1,1-tris(4-hydroxyphenyl)-ethane (1.53 g, 5 mM) in 40 ml ethanol and 40 ml water cooled in ice, KOH (2.2 gr, 39.2 mM) followed by KI (5.8 g, 34.8 mM) and iodine (8.8 g, 34.7 mM) were added. The color turns from violet to brown. The reaction was stirred at room temperature for 3 hours. The mixture was added to crushed ice. Concentrated HCl was added to obtain acidic pH and was treated with thiosulphate solution and worked up. Evaporation gave 5.1 g light brown solid, hexa iodo product followed by trituration in ethanol gave 3 g white solid, 61% yield, mp=230°. RF=0.8 (in 5% MeOH—$CH_2Cl_2$).

NMR $CDCl_3$ δ 7.3 (6H, s), 5.77 (br.s, OH), 1.97 (3H, s, $CH_3$).

Example 10

Repair of DNA Double-Stranded Fragments Using Telomerase

In order to assess telomerase activation and/or expression, a DNA repair assay was conducted. DNA fragments were generated by ionic radiation. All the compounds increased repair. These results indicate that telomerase activity and/or expression provided stability in stress conditions.

Example 11

Figure 8:
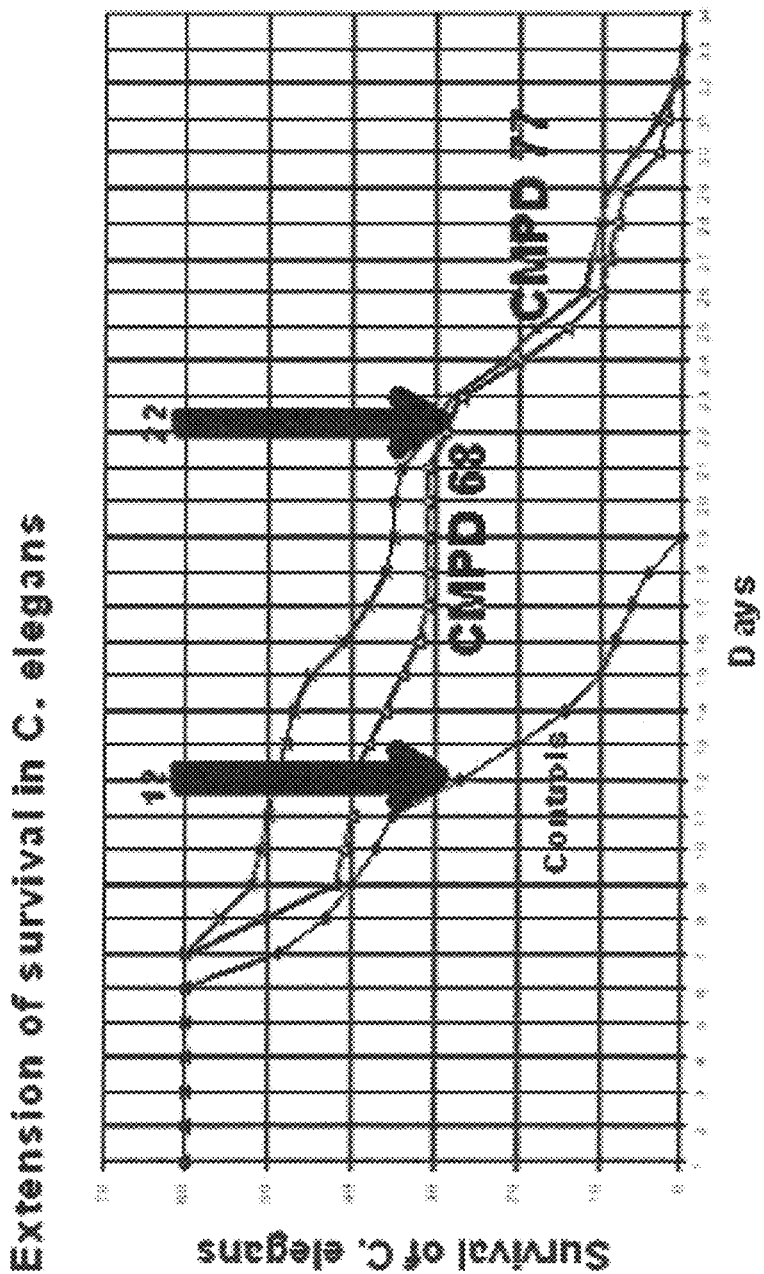
FIG. 8: Lifespan extension of C. elegans by telomerase-activating Compounds 68 and 77.

Effects of Tri-Phenyl Telomerase Activating Compounds on Lifespan Extension with Nematodes Nematodes (C. elegans) were administered tri-phenyl telomerase-activating compounds presented in the following tables, and telomerase activity and/or expression was measured in terms of nematode lifespan extension. Nematodes were grown with the activators at 50 micromolar concentration, and the mean, maximum and half-life for Compound 68 and Compound 77, two representative molecules, was measured versus that of the control (FIG. 8). Values represent mean lifespan.

TABLE 1

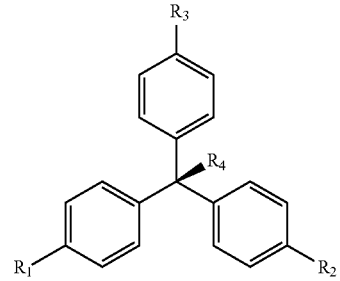

| Compound # | $R_1$ | $R_2$ | $R_3$ | $R_4$ | Lifespan ext. % |
|---|---|---|---|---|---|
| 1 | OH | OH | OH | $CH_3$ | 30 |
| 2 | OAc | OAc | OAc | $CH_3$ | |
| 3 | H | H | H | Cl | |
| 4 | H | H | H | $CH_3$ | |
| 5 | $OCH_3$ | $OCH_3$ | $OCH_3$ | $CH_3$ | 12 |
| 6 | $OCH_3$ | $OCH_3$ | H | $CH_3$ | |
| 7 | $OCH_3$ | H | H | OH | |
| 8 | | | | Cl | |
| 9 | | | | $CH_3$ | |
| 10 | $CH_3$ | H | H | $CH_3$ | −1 |
| 11 | $OCH_3$ | $CH_3$ | $CH_3$ | OH | |
| 12 | | | | Cl | |
| 13 | | | | $CH_3$ | |
| 14 | $OCH_3$ | $OCH_3$ | $CH_3$ | OH | |
| 15 | | | | Cl | |
| 16 | | | | $CH_3$ | |
| 17 | $OCH_3$ | $OCH_3$ | F | OH | |
| 18 | | | | Cl | |
| 19 | | | | $CH_3$ | |
| 20 | $CH_3$ | $CH_3$ | $CH_3$ | OH | |
| 21 | | | | Cl | |
| 22 | | | | $CH_3$ | 21 |
| 23 | 1-naphtyl | $OCH_3$ | OEt | OH | |
| 24 | | | | Cl | |
| 25 | | | | $CH_3$ | |
| 26 | 1-naphtyl | 1-naphtyl | 1-naphtyl | OH | |

TABLE 1-continued

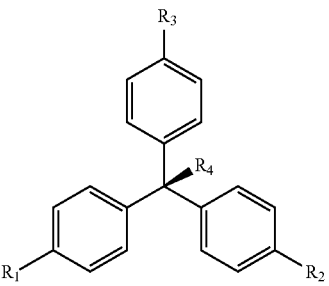

| Compound # | R₁ | R₂ | R₃ | R₄ | Lifespan ext. % |
|---|---|---|---|---|---|
| 27 | | | | Cl | |
| 28 | | | | CH₃ | |
| 29 | 9-fluorene | | OCH₃ | OH | |
| 30 | 9-fluorene | | OCH₃ | Cl | |
| 31 | | | | CH₃ | 23 |
| 31 | 9-xanthene | | H | Cl | |
| 33 | | | | CH₃ | −26 |
| 34 | Satu.7 ring | | OCH₃ | OH | |
| 35 | | | | Cl | |
| 36 | | | | CH₃ | |
| 37 | Unsatu.7 ring | | OCH₃ | OH | |
| 38 | | | | Cl | |
| 39 | | | | CH₃ | |
| 40 | | | | | |
| 41 | Tol Bz | Tol Bz | Tol Bz | CH₃ | |
| 42 | OCH₂CO OEt | OCH₂CO OEt | OCH₂CO OEt | CH₃ | −7 |
| 43 | OCH₂CO OH | OCH₂CO OH | OCH₂CO OH | CH₃ | |
| 44 | H | H | H | Cl | |
| 45 | H | H | H | CH₃ | |
| 46 | H | H | H | OEt | |
| 47 | H | H | H | O-iso propyl | |
| 48 | H | H | H | O-n butyl | |
| 49 | H | H | H | CH₃ | 16 |
| 50 | 3-INDOL | 3-INDOL | OCH₃ | H | 4 |
| 51 | 3-INDOL | 3-INDOL | OCH₃ | CH₃ | |
| 52 | Des tetra dimethyl amino | | | | −25 |
| 53 | 4-Py | OH | OH | CH₃ | 13 |
| 54 | 3-PY | OH | OH | CH₃ | 15 |
| 55 | 4-Py | H | H | CH₃ | |
| 56 | 4-Py | CH₃ | CH₃ | CH₃ | |
| 57 | 4-Py | OCH₃ | OCH₃ | CH₃ | |
| 58 | 4-Py | OCH₃ | OH | CH₃ | |
| 59 | | | | | |

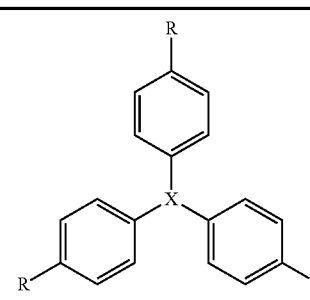

| Compound # | R | X | Lifespan % |
|---|---|---|---|
| 60 | OH | P | −2 |
| 61 | OH | P=O | 30 |
| 62 | OCH₃ | P | 29 |
| 63 | OCH₃ | P=O | 0 |
| 64 | H | P | 19 |
| 65 | CH₃ | P | 42 |
| 66 | Br | N | 19 |

| Compound # | R₁ | R₂ | R₃ | Lifespan % |
|---|---|---|---|---|
| 67 | Cl | OH | Cl | |
| 68 | Br | OH | Br | 13 |
| 69 | Br | OH | H | −5 |
| 70 | Br | OCH₃ | Br | 41 |
| 71 | NO₂ | OH | H | 8 |
| 72 | NO₂ | OCH₃ | H | 4 |
| 73 | I | OCH₃ | I | −7 |
| 74 | I | OH | H | |
| 75 | OH | OH | OH | |
| 76 | NH₂ | OH | H | |
| 77 | CH₂— Dimethyl amino | OH | CH₂— Dimethyl amino | 43 |
| 78 | CH₂— Methyl piperazine | OH | CH₂— Methyl piperazine | 36 |
| 79 | CH₂OEt | OH | CH₂OEt | 16 |
| 80 | CH₂OAc | OAc | CH₂OAc | |
| 81 | CH₂— pyrrolidine | OH | CH₂— pyrrolidine | |
| 82 | CH₂— morpholine | OH | CH₂— morpholine | |
| 83 | CH₂— piperidine | | CH₂— piperidine | |
| 84 | CH₂— diethyl amine | | CH₂— diethyl amine | |

Example 12

Effects of Tri-Phenyl Telomerase Activating Compounds on Human Glioblastoma Cells Compounds 1, 62, 68, 77 and 79 (referred to in the tables above) were examined for telomerase activation and/or expression in glioblastoma cells. Compound 79 and 68 were synthesized as described hereinabove. Compounds 1 and 62 are commercially available. One µM of nuclear cell proteins (as the source of telomerase) were added to a specific reaction mixture of telomerase and a telomerase repeat amplification (TRAP) assay was performed in the absence or presence of telomerase activators (Compounds 79, 68, 1 and 62). The reaction products were analyzed on PAGE followed by autoradiography. The % of telomerase activity/expression was calculated.

U-251 gliobastoma cells were treated with different concentrations of compounds of the present invention for 1 or 3 hours. The culture medium was removed and the cells were washed several times with PBS. Chaps nuclear extract was performed by standard methodology and telomerase activity was determined by TRAP using radioactive nucleotides. A representative picture of several experiments demonstrating the products of telomerase activity observed by the TRAP assay is shown in FIG. 1A. Cells were treated with Compound 68 at 1 (lanes 2 and 4), or 0.25 µM (lanes 3 and 5) for 1 (lanes 2-3) or 3 (lanes 4-5) hours, respectively. Lane 1 shows vehicle treatment only. Quantification of telomerase activity from multiple experiments was performed using a β-scintillation counter by measuring the total radioactive labeling of telomerase products, and telomerase activity in each sample was calculated relative to the internal standard. The percent telomerase activation (from the control cells treated with the vehicle only) was determined for the compounds of the present invention (FIG. 1B). Compounds of the present invention significantly increased the activity of telomerase in treated cells and the level of activation was dependent on the nature of the compound, the concentration and the time of exposure of the cells to the compounds of the present invention.

Figure 2:
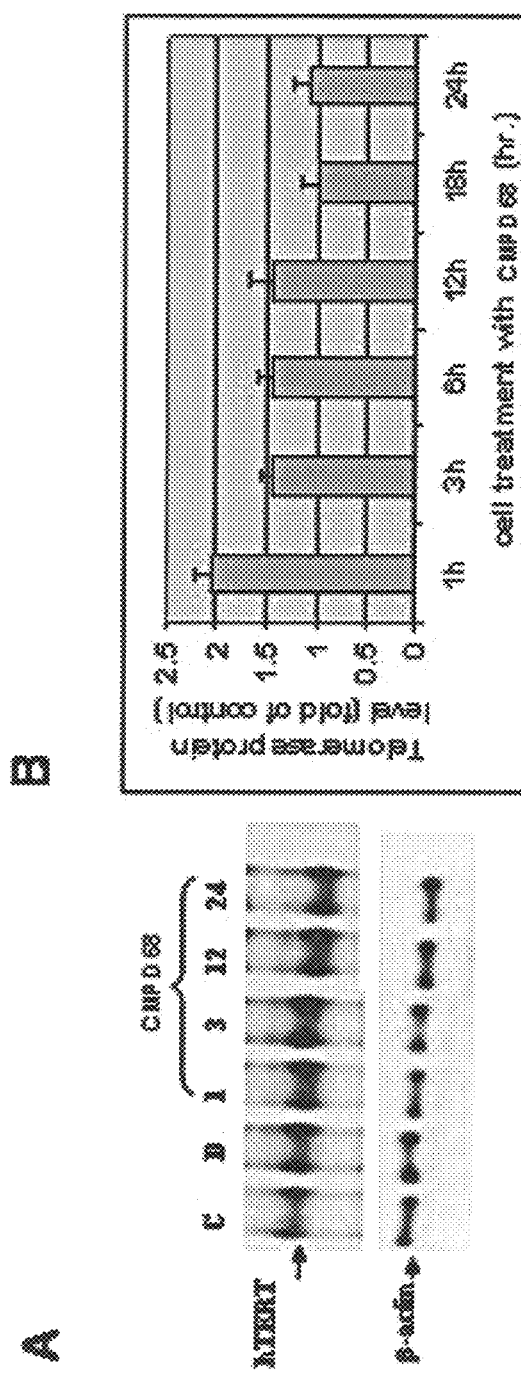
FIG. 2: Time-dependent increase of telomerase protein level by compounds of the present invention. A. Western blot analysis with anti-human telomerase antibody. B. Quantification of telomerase protein level.

The effect of compounds of the present invention on the level of telomerase protein and of long-term treatment of a single dose of Compound 68 on telomerase was tested by exposing cells for various intervals (3-24 h) to 1 µM of the compound and detecting telomerase protein level by western blot analysis with anti-telomerase antibody. Compound 68 increased telomerase protein level in treated cells (FIG. 2A). A time-dependent increase in telomerase was observed, with activation peaking at 1-3 h of treatment, and then gradually decreasing. The level of telomerase activity was only slightly higher compared to that found in vehicle-treated cells after 24 h (FIG. 2B). No changes in the level of β-actin protein (lower panel) or other nuclear enzymes such as topoisomerase I were observed, suggesting that a single dose causes a fast, specific activation of telomerase, although this activation is transient and the level of telomerase returned to its basal value 24 h after treatment, indicating an ability of compounds of the present invention to control telomerase activation.

Figure 3:
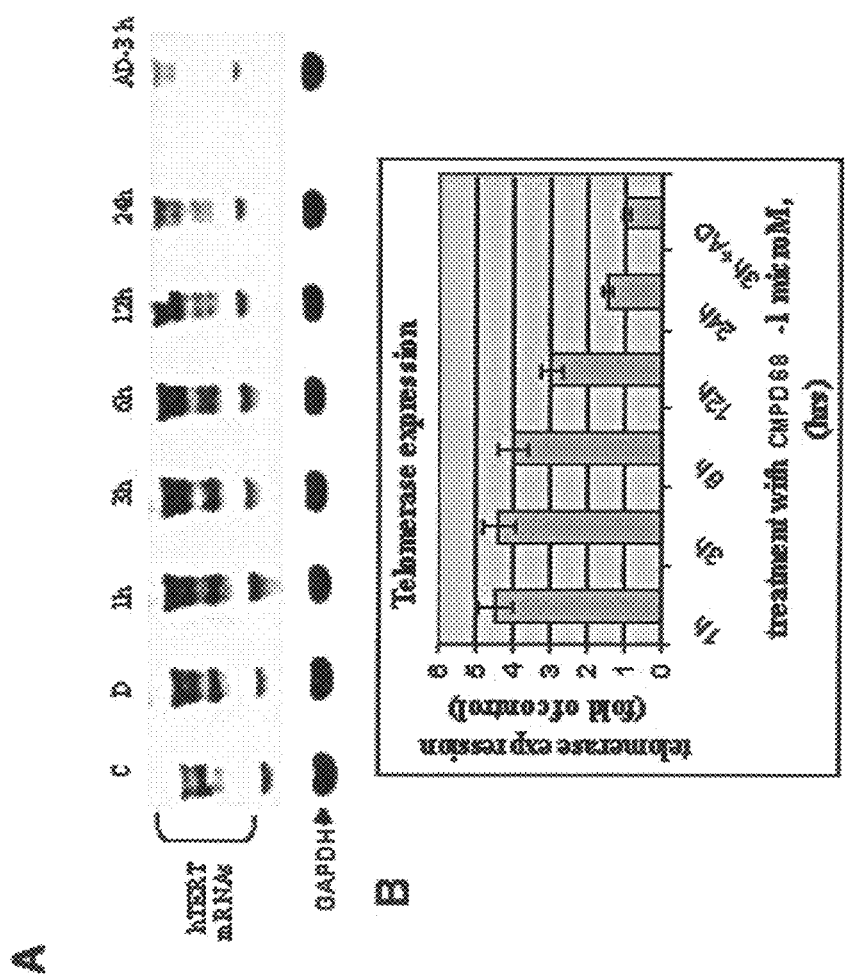
FIG. 3: Compound 68 increases the expression of telomerase RNA. A. Northern blot analysis using hTERT-specific cDNA probe. AD is actinomycin D. B. Quantification of RNA level.

Experiments were also performed to determine the effect of compounds of the present invention on the telomerase mRNA level (including the full and spliced variant telomRNAs). Cells were treated with a single dose of 1 mM Compound 68 for various intervals (1-24 h). Total RNA extracts were prepared, and equal RNA concentrations were analyzed by northern blotting with a specific hTERT probe. FIG. 3A shows the telomerase full-length and splice variant mRNAs in the control untreated cells (lanes 1,2). The level of the full-length mRNA as well as the splice variant RNAs significantly increased with time in cells treated with compounds of the present invention (up to 4.5-fold of control) (FIG. 3B, lanes 3-7). The increased expression of telomerase was specific since no effect on GAPDH mRNA was observed (lower panel). Addition of actinomycin D (an RNA transcription inhibitor) during treatment with compounds of the present invention (for 3 h) abolished the activation of telomerase expression (FIGS. 3A and B, compare lane 8 to 4), suggesting that compounds of the present invention activate the expression of the telomerase gene.

Example 13

Effects of Compounds of the Present Invention on Human Mesenchymal Stem Cells

Figure 4:
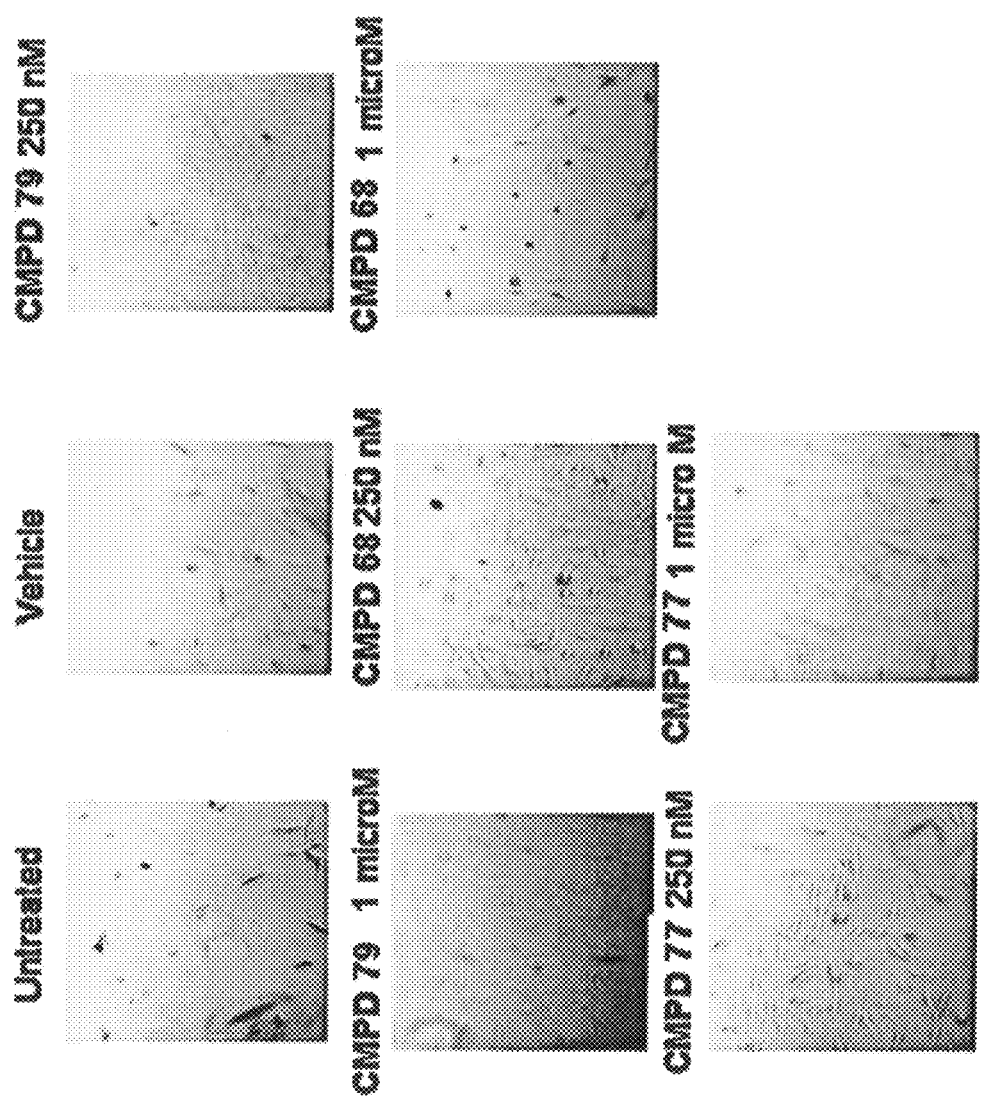
FIG. 4: The effect of treatment with compounds of the present invention on survival and proliferation of hMSC.

Human mesenchymal stem cells were isolated by iliac crest aspiration and grown in cell culture for 6 months (passage 19) prior to observing a significant decrease in cell growth. Compounds of the present invention were added directly to the culture medium daily for 3 days. Significant survival and proliferation of the hMSC was observed upon treatment with various compounds of the present invention (FIG. 4).

Figure 5:
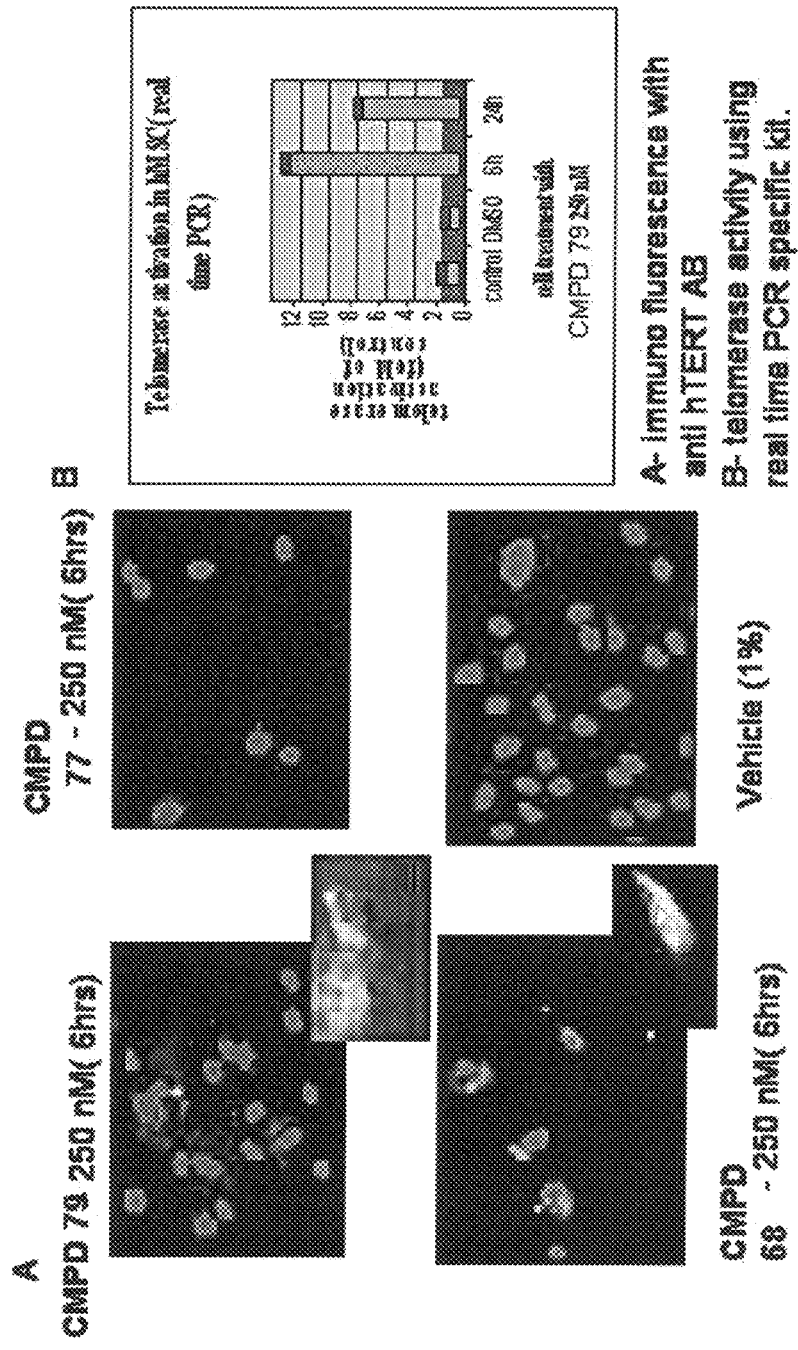
FIG. 5: Activation of telomerase expression in hMSC by compounds of the present invention. A.—hMSC were treated with 250 nM of Compounds 79, 77 and 68 for 6 hours. Immunofluorescence was performed with anti-hTERT antibody (red) and the nucleus was stained with DAPI (blue). B. hMSC treated with compound 79 for 6 and 24 h. Telomerase activity was measured by real time PCR using a quantitative telomerase detection kit (Allied Biotech Inc., USA).

The possibility that compounds of the present invention enhance hMSC survival and proliferation by activation of TERT was examined by culturing hMSC (p 3) in a tissue culture chamber slide at $17 \times 10^3$ cells/well for 60 h. Compounds of the present invention were added for 6 h with fresh medium. Immunofluorescence with anti-hTERT antibody (first antibody) and cy3 fluorescent secondary antibody was carried out. The nucleus was stained with DAPI. Compounds of the present invention activated telomerase expression in hMSC (FIG. 5). Expression of telomerase protein was seen in both cytoplasm and nucleus. Degree of activation of telomerase expression was Compound 68>79>77. Quantification of telomerase activity in hMSC was performed by Real time PCR (Quantification telomerase detection kit) in nuclear extracts derived from hMSC treated with compound 79 (250 nM) for 6 or 24 h. Compound 79 enhanced telomerase activity in hMSC by 12- or 6-fold in a time-dependent manner (FIG. 5B).

Example 14

Effects of Compounds of the Present Invention on Human Keratinocytes

Figure 6:
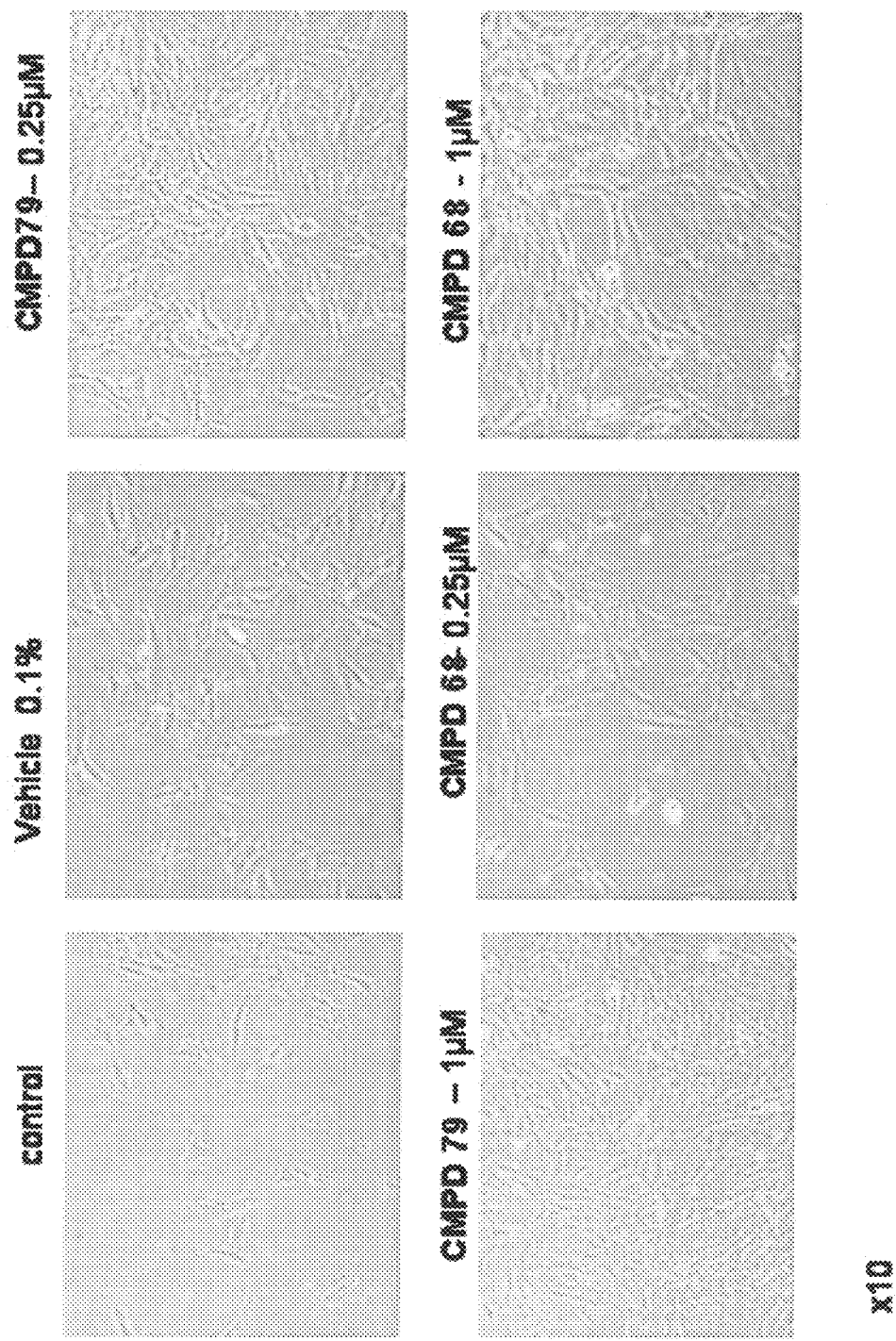
FIG. 6: The effect of compounds of the present invention on senescent human keratinocytes in vitro.

Human keratinocytes which had lost their ability to proliferate (in their fifth passage) were obtained from a local skin bank and treated with Compound 68 for 24 h. Cell viability, cell number and morphology was examined. Cells treated with compounds of the present invention exhibited significant (2-4-fold) cell proliferation and viable cells were observed (FIG. 6). Compound 79 exhibited a better cell survival effect than Compound 68. These results support a role for the compounds of the present invention in skin transplantation, wound healing, chronic skin ulcers and other skin conditions.

Example 15

Figure 7:
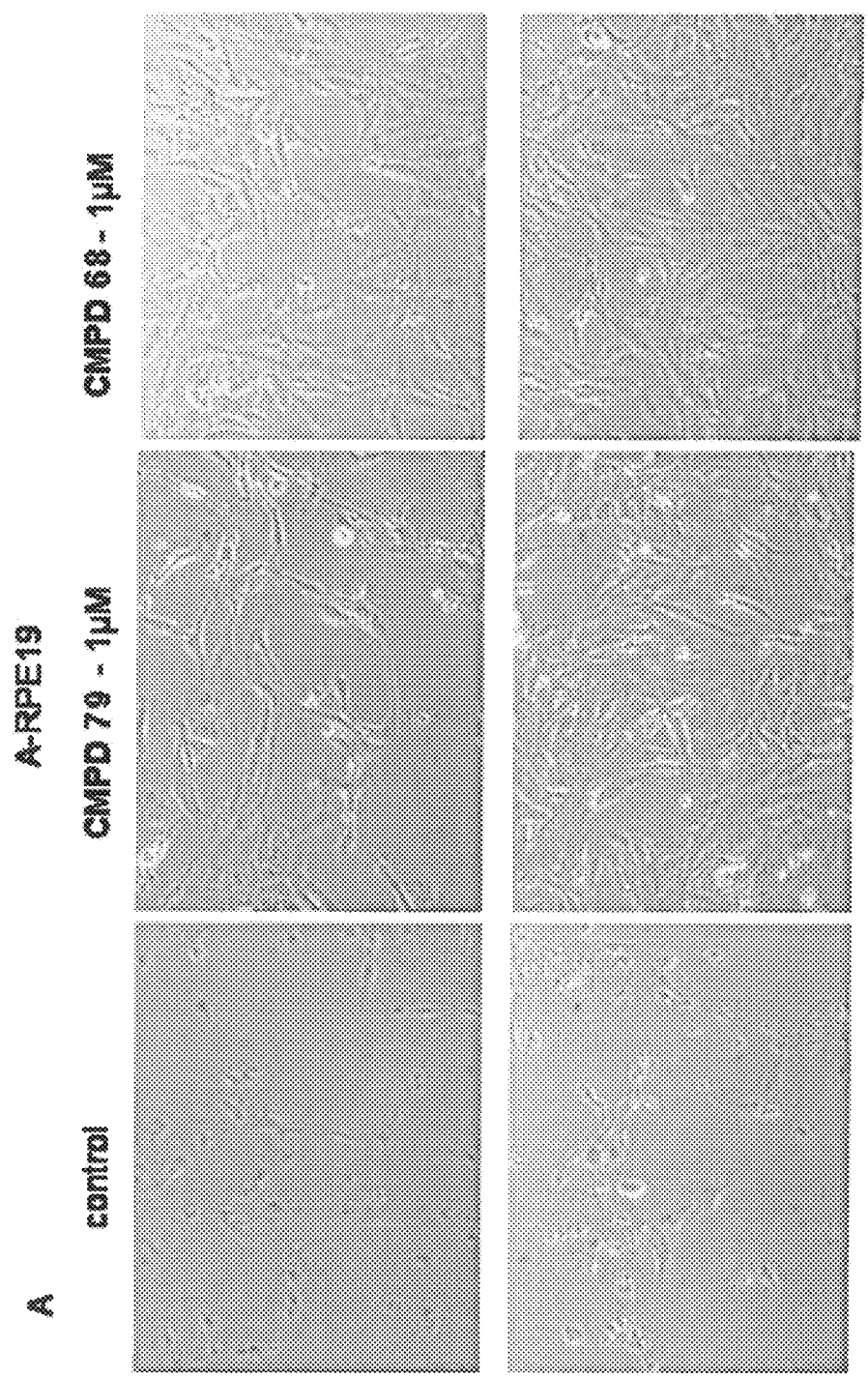
FIG. 7: A. The effect of compounds of the present invention on human retinal pigmented epithelial cells under oxidative stress. B. The effect of compounds on telomerase activity in RPE cells (measured by a quantitative telomerase detection kit-real time PCR).
Figure 7:
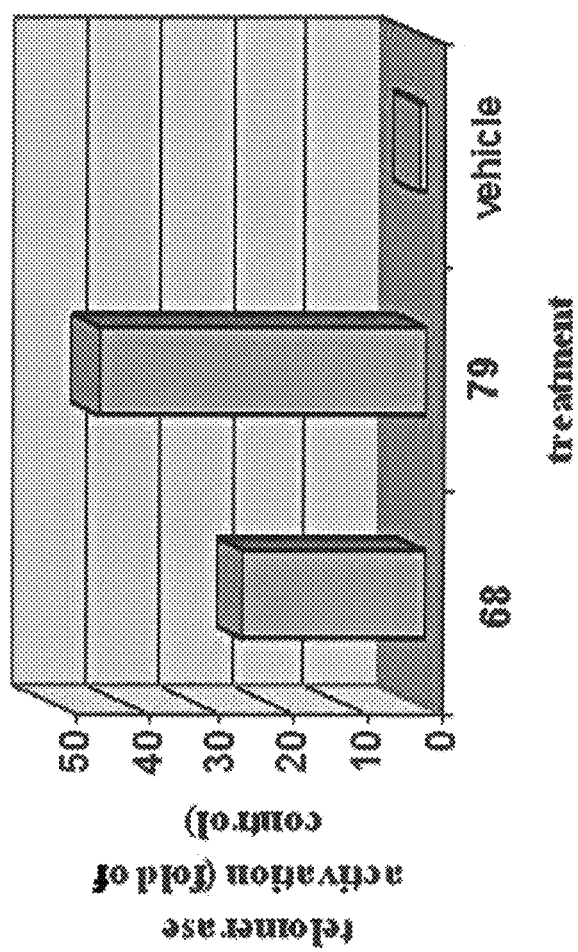

Effects of Compounds of the Present Invention on Human Retinal Pigmented Epithelial Cells Chronic exposure of human retinal pigmented epithelial (RPE) cells to oxidative stress predisposes them to the development of age-related macular degeneration (AMD). Human RPE cells were exposed to oxidative stress by treatment with $H_2O_2$ (1 mM) for 24 hours, and $H_2O_2$ (0.5 mM) for another 24 hours. The cells were then treated daily for two days with the indicated compounds in the absence of $H_2O_2$. Increased cell growth was observed as a consequence of treatment with the compounds (FIG. 7A). Telomerase activity was enhanced in RPE cells treated with compounds 68 and 79 by 30- and 50-fold, respectively (FIG. 7B). These results suggest a role for the compounds of the present invention in treating macular degeneration and other retinal diseases.

Example 16

Extension of Survival in C. Elegans

Survival of the C. elegans, a nematode that normally survives for 12-14 days, represents an acceptable model for studying life extension. Nematodes were administered triphenyl telomerase-activating compounds and their effect on the nematode lifespan extension was determined. Nematodes were grown with the activators at a concentration of 50 micromolar, and mean, maximum and half-life were measured in comparison with untreated controls. Lifespan increased by 13-43% (Table 2), and the median lifespan increased approximately 2-fold (from 12 days to 22 days, as shown in FIG. 8).

TABLE 2

Extension of survival of C. elegans by telomerase compounds

| Compound no. | Lifespan extension (%) |
|---|---|
| 61 | 30 |
| 62 | 29 |
| 68 | 13 |
| 77 | 43 |
| 78 | 36 |
| 79 | 16 |

Example 17

Figure 9:
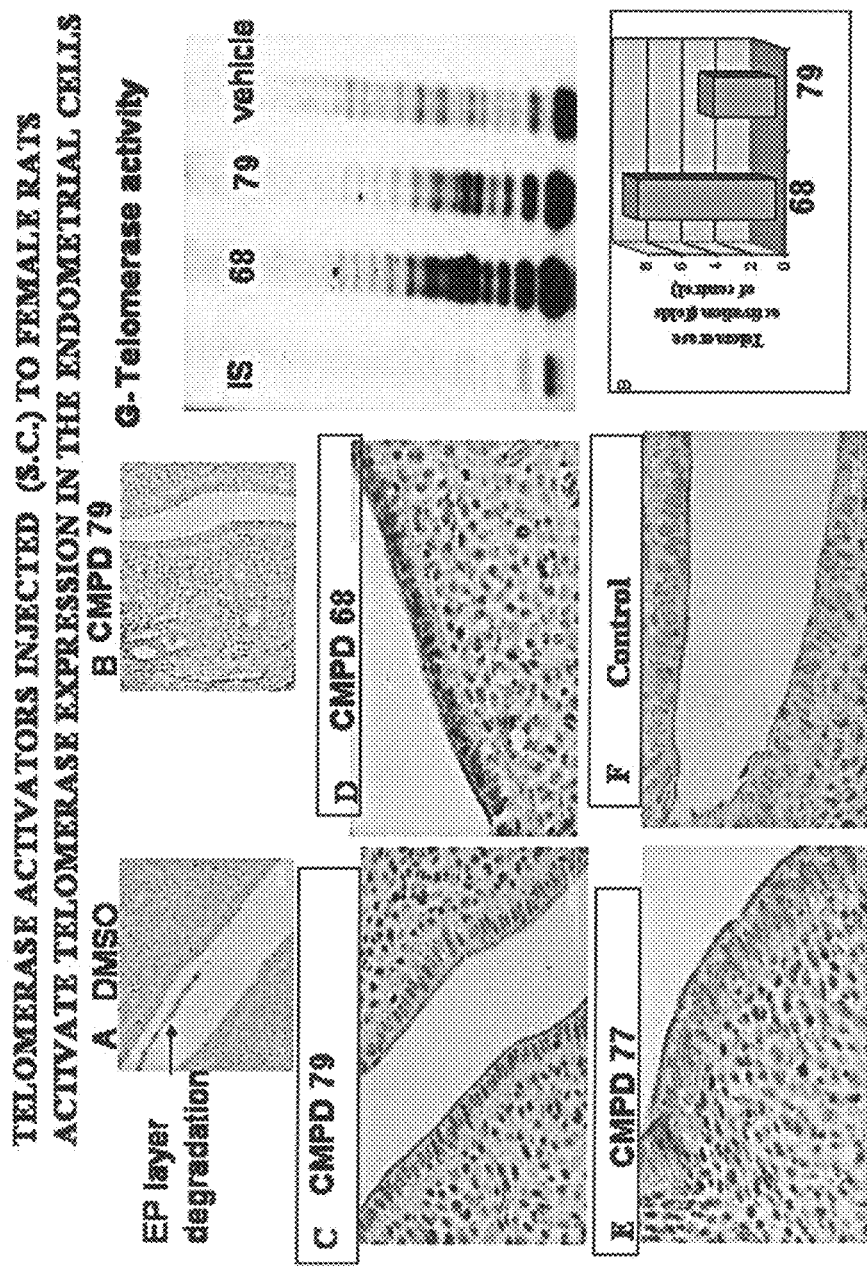
FIG. 9: Activation of telomerase expression by compounds of the present invention in rat endometrial cells. A,B. Histological analysis. C-F. Immunohistochemical analysis with specific anti-hTERT antibody. G. Telomerase activity in nuclear extracts derived from endometrium of rats injected with compounds of the present invention. G(B) Telomerase activity in nuclear extracts derived from endometrium of rats injected with compounds of the present invention measured by real time PCR using a quantitative telomerase detection kit (Allied Biotech Inc., USA).

Activation of Telomerase Expression by Compounds of the Present Invention in Rat Endometrial Cells Female rats in diestrus (the stage at which the epithelial layer in the rat endometrium undergoes degradation) were injected subcutaneously with 6 mg/kg of Compound 68, or with a vehicle. The rats were sacrificed 24 h later and endometrial sections were prepared from the uterine horns of treated and untreated rats and analyzed by histological procedures and by immunohistochemical staining Endometrial slices were stained by hematoxylin-eosin. Treatment with compounds of the present invention prevented the degradation of the endometrial epithelial layer. In addition, morphologically, the endometrial tissue resembled the structure of the proliferating stages (proestrus and estrus) (FIG. 9A,B). Activation of telomerase expression in the endometrial cells of treated rats was examined by immunohistochemistry with anti-telomerase antibody (FIG. 9C-F). There was a significant increase in the staining of telomerase in the endometrial tissue of rat injected with compounds of the present invention, especially in the epithelial layers of the endometrial lumen and the epithelial layer of the secreting glands (compare FIGS. 9C and D, E and F). In addition, telomerase activity was measured in nuclear extracts derived from the endometrium of the various treatment groups. A significant 4-8-fold increased in the activity of telomerase was observed in the rats injected with compounds of the present invention (FIG. 9G), indicating that compounds of the present invention injected subcutaneously in the neck reached the endometrial tissue, activated telomerase and caused tissue proliferation. These data support a role for the compounds of this invention activating telomerase in animals and affecting the proliferation of a tissue in vivo. In some embodiments of the invention, the data support a role for the treatment of endometriosis with the compounds of this invention.

Example 18

Figure 10:
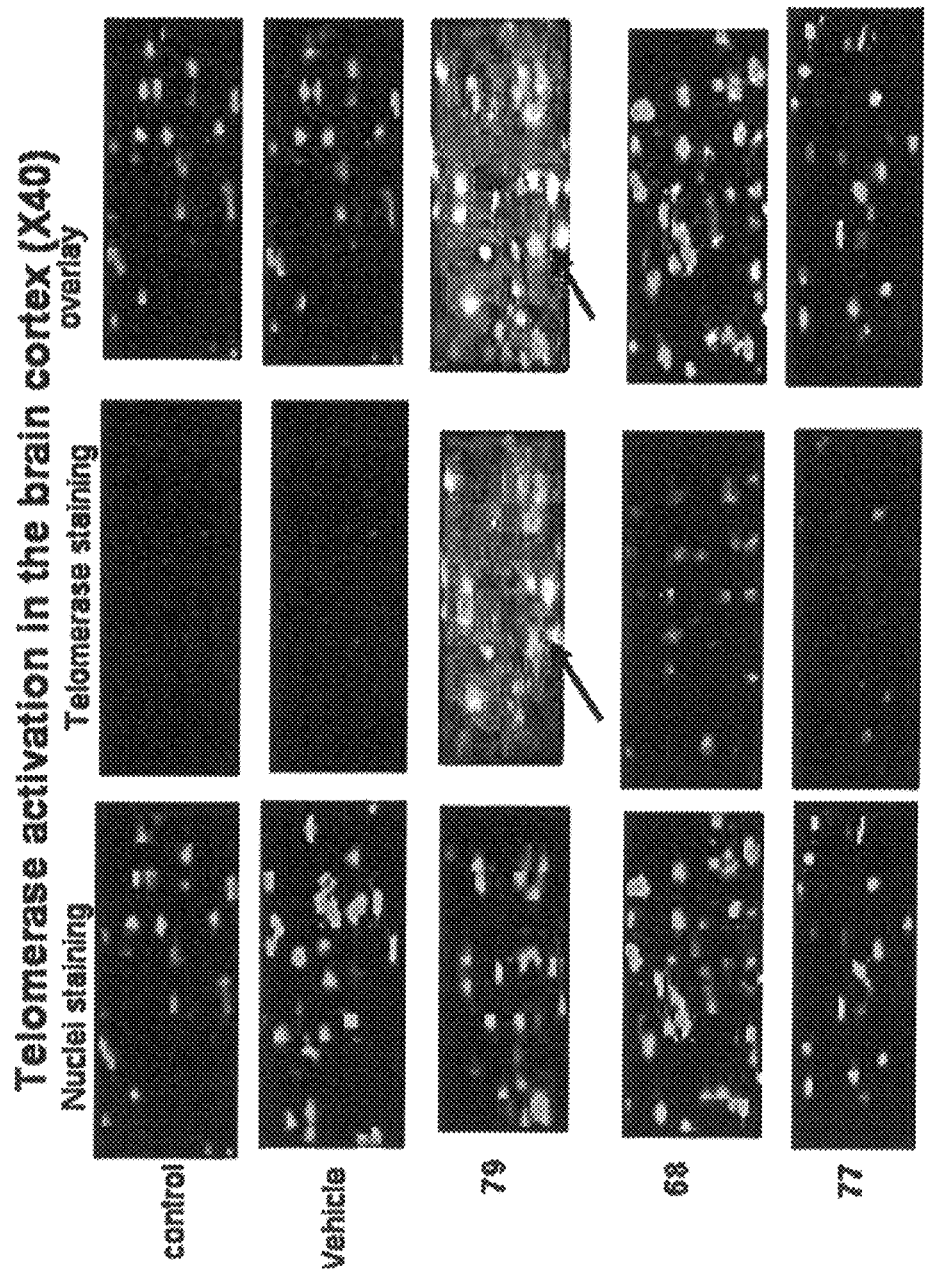
FIG. 10: Telomerase activation of rat brain cortex cells by compounds of the present invention.
Figure 11:
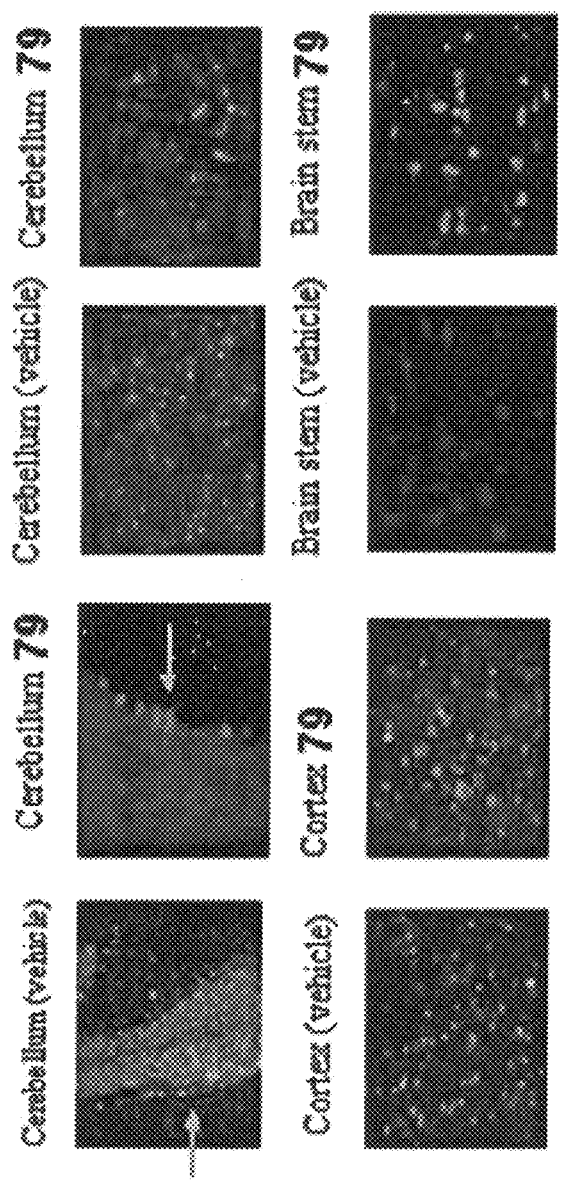
FIG. 11: Telomerase activation of mouse CNS by compounds of the present invention.

Telomerase Activation of Rat Brain Cortex Cells by Compounds of the Present Invention The effect of compounds of the present invention injected subcutaneously into female rats and adult male mice on telomerase expression in various regions of the brain was examined. Co-localization of telomerase and DAPI (DAPI or 4',6-diamidino-2-phenylindole), a DNA-binding fluorescent stain demonstrated activation and/or expression in these cells as a consequence of treatment. A very low expression of telomerase was observed in specific cells in various areas of the CNS (FIGS. 10 and 11). Injections of Compounds 79 and 77 into rat significantly activated the expression of telomerase in the brain cortex, but Compound 68 did not, indicating that Compounds 79 and 77, but not Compound 68, may cross the blood-brain barrier (BBB) (FIG. 10).

Compound 79 was injected subcutaneously into three-month-old male mice. The mice were sacrificed 24 h later and the cortex, cerebellum, hippocampus, hypothalamus, brain stem and olfactory bulb isolated and subjected to immunofluorescence. A low epxression of telomerase was observed in most of the brain regions examined except for Purkinje cells in the cerebellum (FIG. 11). Injection of compounds of the present invention significantly and dramatically increased telomerase expression in the various brain regions. This activation appeared to be specific for certain neuronal cells. Compound 79, for example, increased telomerase expression in the motor-neuronal cells present in the brain stem.

Figure 12:
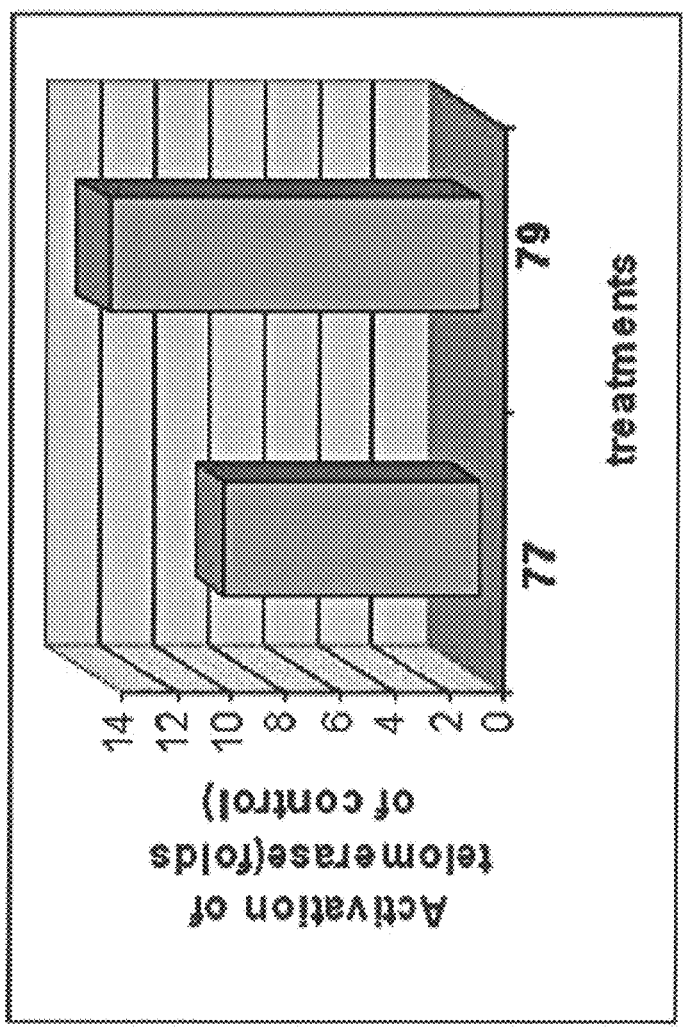
FIG. 12: Telomerase protein is increased in rats treated with compounds of the present invention.

Confirmation of immunofluorescence results was obtained by examining the level of TERT protein enzyme in nuclear protein extracts derived from brains removed from rats treated or untreated with compounds of the present invention. Western blot analysis using specific anti-hTERT antibody was performed and telomerase activation (%) was determined and calculated relative to the results obtained with the vehicle. A significant increase (9-13-fold) in telomerase protein was observed in rat brain cortex cells treated with compounds of the present invention (FIG. 12), supporting a role for the use of compounds of the present invention in treating brain-related diseases.

Example 19

Prevention of Glutamate-Induced Apoptosis in Mouse Cerebellum

Figure 13:
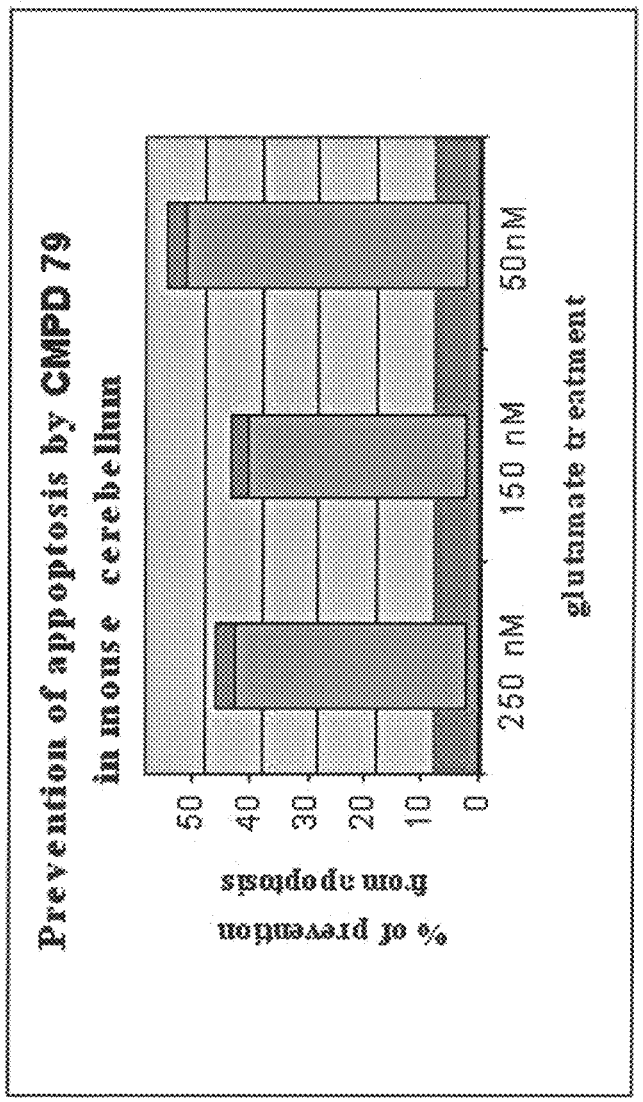
FIG. 13: Prevention of glutamate-induced apoptosis in mouse cerebellum by Compound 79.

The ability of compounds of the present invention to prevent glutamate-induced apoptosis in mouse cerebellum was examined. Mice were injected with 6 mg/kg of Compound 79 or with vehicle only. Mice were sacrificed 24 h after treatment and their brains were removed. Cerebellum slices were prepared and subjected to glutamate treatment at various concentrations for 30 min. Sections were stained with propidium iodide and the number of apoptotic cells was counted and calculated using specific software (Jimage). Prevention of apoptosis in mice treated with compounds of the present invention was calculated as a percentage relative to control mice (FIG. 13). This supports a role for compounds of the present invention in treating seizures, stroke, Alzheimer's disease, epilepsy, schizophrenia, and alcohol and opiate addition.

Example 20

Figure 14:
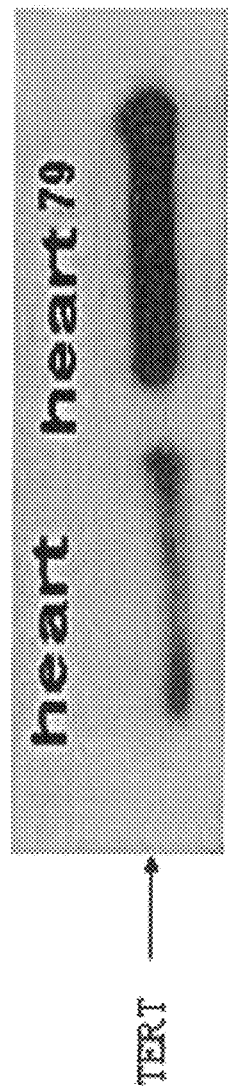
FIG. 14: Telomerase expression is activated in mouse heart by Compound 79.

Telomerase Activation of Mouse Heart Cells by Compounds of the Present Invention The activation of telomerase by compounds of the present invention in heart protein extracts derived from one mouse was measured (FIG. 14). There was a significant increase in the heart telomerase expression following injection of Compound 79. This supports a role for compounds of the present invention in treating infarct, ischemia, myocarditis, etc.

Example 21

Prevention of Drug Damage to Embryos by Compounds of the Present Invention

Figure 15:
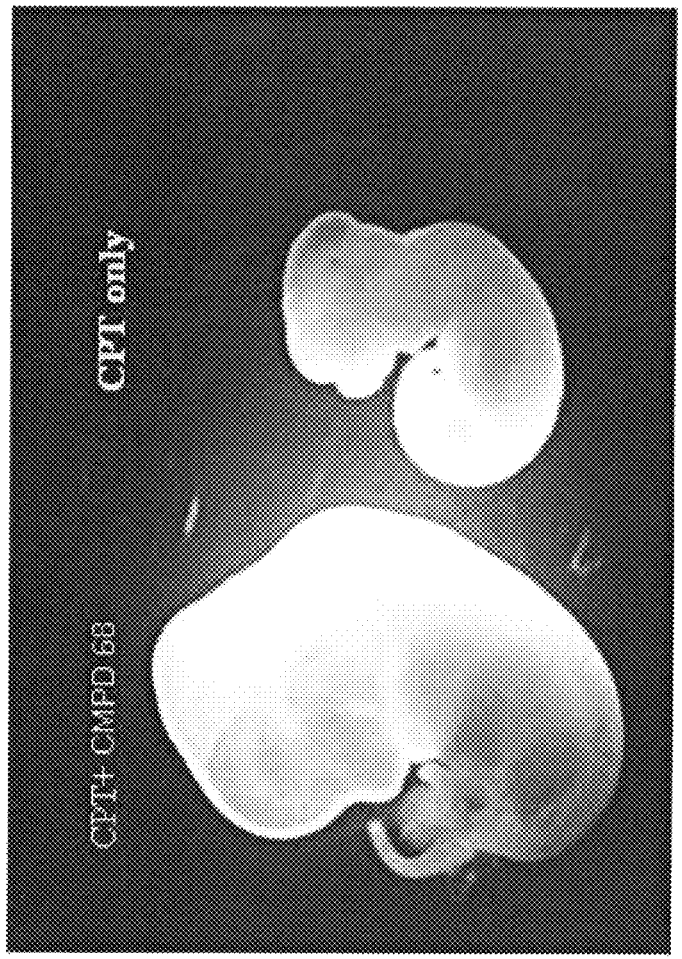
FIG. 15: Compound 68 prevents the effect of damaging drugs on embryo development in rats.

The ability of compounds of the present invention to prevent the damaging effects of drugs on embryonic development was examined in rats. Female rats were treated with camptothecin (CPT) (5 mg/kg), an anti-cancer drug, and then injected with Compound 68 (6 mg/kg) or vehicle (0.1%). Embryos were removed at days 14-15 of pregnancy and examined for damage. Embryos treated with both CPT and Compound 68 developed normally, while embryos treated with CPT only showed evidence of abnormal development (FIG. 15).

Example 22

Effect of Compounds of the Present Invention on BCL1 Tumorigenicity (BALB/c×C57BL/6)F1 mice were inoculated with $10^5$ murine B-cell leukemia lymphoma (BCL1) cells. Splenomegaly and lymphocytosis (leukemia) developed in all controls and in mice treated with telomerase-activating compounds (40 or 80 mg/kg).

TABLE 3

| Experimental Group | Survival Median (range) |
|---|---|
| BCL1 only | 29 (21-35) |
| BCL1 + Compound 77 10 mM | 26 (22-41) |

Telomerase-activating compounds did not enhance the development of leukemia and did not shorten the survival of mice which were inoculated with leukemia. The telomerase-activating compounds of the present invention did not facilitate progression of existing cancer, nor did long-term administration of the compounds result in development of cancer.

Example 23

Effect of Compounds of the Present Invention on Graft-Versus-Host Disease (GVHD) as a Representative T Cell Function (BALB/c×C57BL/6)F1 mice were inoculated with $30\times10^6$ C57BL/6 spleen cells for induction of GVHD. Mice treated with Compound 77 exhibited more severe signs of acute GVHD, as demonstrated by weight loss as compared with untreated controls. These results suggest that compounds of the present invention may be used as a powerful adjuvant.

Example 24

Effect of Compounds of the Present Invention on Graft-Versus-Leukemia Disease (GVL) as a Representative Example of Immunotherapy by T Cells (BALB/c×C57BL/6)F1 mice were inoculated with $10^6$ BCL1 following total body irradiation 400 cGy to allow engraftment of allogeneic lymphocytes for induction of graft-versus-leukemia (GVL) effects medicated by $30\times10^6$ C57BL/6 spleen cells. Survival of untreated controls ranged from 21-35 days (median 29). Survival of mice treated with allogeneic stem cells ranged from 13-22 days since the leukemia activated a severe GVHD. In contrast, survival of mice treated with allogeneic stem cells and compounds of the present invention ranged from 37-74 days, with one mouse surviving 125 days. This supports a role for the compounds of the present invention in treating leukemia.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of stimulating or increasing telomerase expression or activity in a cell or tissue of a subject, said method comprising contacting said cell or tissue of said subject, with an effective amount of a compound represented by the structure of the following formula:

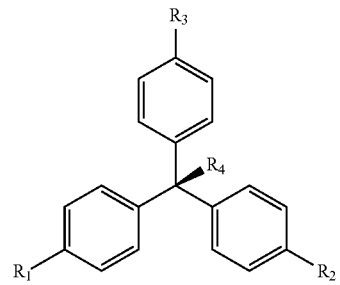

wherein the compound has groups $R_1$, $R_2$, $R_3$ and $R_4$ defined in the table below:

| Compound # | $R_1$ | $R_2$ | $R_3$ | $R_4$ |
|---|---|---|---|---|
| 2 | OAc | OAc | Oac | $CH_3$ |
| 3 | H | H | H | Cl |
| 4 | H | H | H | $CH_3$ |
| 5 | $OCH_3$ | $OCH_3$ | $OCH_3$ | $CH_3$ |
| 6 | $OCH_3$ | $OCH_3$ | H | $CH_3$ |
| 7 | $OCH_3$ | H | H | OH |
| 9 | $OCH_3$ | H | H | $CH_3$ |
| 10 | $CH_3$ | H | H | $CH_3$ |
| 11 | $OCH_3$ | $CH_3$ | $CH_3$ | OH |
| 12 | $OCH_3$ | $CH_3$ | $CH_3$ | Cl |
| 13 | $OCH_3$ | $CH_3$ | $CH_3$ | $CH_3$ |
| 14 | $OCH_3$ | $OCH_3$ | $CH_3$ | OH |
| 15 | $OCH_3$ | $OCH_3$ | $CH_3$ | Cl |
| 16 | $OCH_3$ | $OCH_3$ | $CH_3$ | $CH_3$ |
| 18 | $OCH_3$ | $OCH_3$ | F | Cl |
| 19 | $OCH_3$ | $OCH_3$ | F | $CH_3$ |
| 22 | $CH_3$ | $CH_3$ | $CH_3$ | $CH_3$ |
| 23 | 1-naphtyl | $OCH_3$ | Oet | OH |
| 24 | 1-naphtyl | $OCH_3$ | Oet | Cl |
| 25 | 1-naphtyl | $OCH_3$ | Oet | $CH_3$ |
| 26 | 1-naphtyl | 1-naphtyl | 1-naphtyl | OH |
| 27 | 1-naphtyl | 1-naphtyl | 1-naphtyl | Cl |
| 28 | 1-naphtyl | 1-naphtyl | 1-naphtyl | $CH_3$ |
| 29 | 9-fluorene | 1-naphtyl | $OCH_3$ | OH |
| 30 | 9-fluorene | 1-naphtyl | $OCH_3$ | Cl |
| 31 | 9-fluorene | 1-naphtyl | $OCH_3$ | $CH_3$ |
| 32 | 9-xanthene | 1-naphtyl | H | Cl |
| 33 | 9-xanthene | 1-naphtyl | H | $CH_3$ |

-continued

| Compound # | R₁ | R₂ | R₃ | R₄ |
|---|---|---|---|---|
| 34 | Satu.7 ring | 1-naphtyl | OCH₃ | OH |
| 35 | Satu.7 ring | 1-naphtyl | OCH₃ | Cl |
| 36 | Satu.7 ring | 1-naphtyl | OCH₃ | CH₃ |
| 37 | Unsatu.7 ring | 1-naphtyl | OCH₃ | OH |
| 38 | Unsatu.7 ring | 1-naphtyl | OCH₃ | Cl |
| 39 | Unsatu.7 ring | 1-naphtyl | OCH₃ | CH₃ |
| 41 | Tol Bz | Tol Bz | Tol Bz | CH₃ |
| 42 | OCH₂COOEt | OCH₂COOEt | OCH₂COOEt | CH₃ |
| 46 | H | H | H | OEt |
| 47 | H | H | H | O-iso propyl |
| 48 | H | H | H | O-n butyl |
| 50 | 3-INDOL | 3-INDOL | OCH₃ | H |
| 51 | 3-INDOL | 3-INDOL | OCH₃ | CH₃ |
| 52 | Des tetra dimethyl amino | 3-INDOL | OCH₃ | CH₃ |
| 55 | 4-Py | H | H | CH₃ |
| 56 | 4-Py | CH₃ | CH₃ | CH₃ |
| 57 | 4-Py | OCH₃ | OCH₃ | CH₃. |

2. A method of stimulating or increasing telomerase expression or activity in a cell or tissue of a subject, said method comprising contacting said cell or tissue of said subject, with an effective amount of a compound represented by the structure of the following formula:

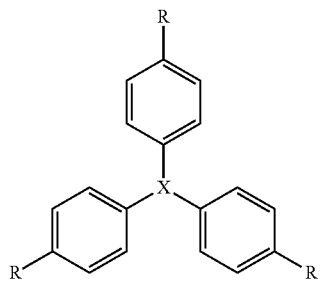

wherein the compound is a compound having groups X and R as defined in the table below:

| Compound # | R | X |
|---|---|---|
| 60 | OH | P |
| 61 | OH | P=O |
| 62 | OCH₃ | P |
| 63 | OCH₃ | P=O |
| 64 | H | P |
| 65 | CH₃ | P |
| 66 | Br | N. |

3. The method of claim 1, wherein said cell or tissue is contacted with the compound of claim 1 in a pharmaceutical acceptable carrier.

4. The method of claim 2, wherein said compound is represented by the structure of formula XVI:

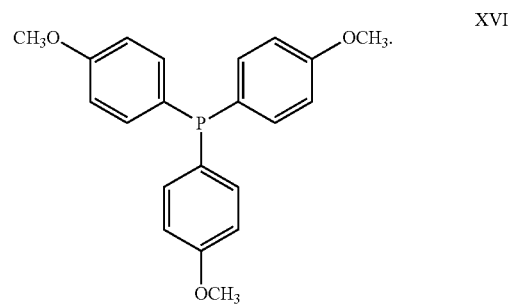

5. A method of stimulating or increasing telomerase expression or activity in a cell or tissue of a subject, said method comprising contacting said cell or tissue of said subject, with an effective amount of a compound represented by the structure of the following formula:

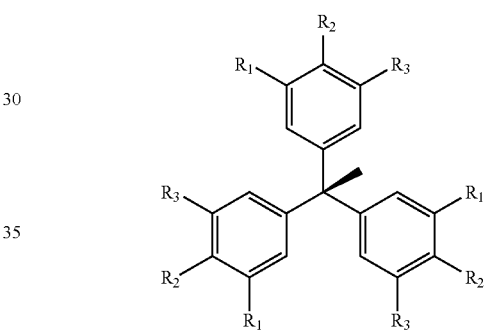

wherein the compound is a compound having groups R₁, R₂ and R₃ as defined in the table below:

| Compound # | R₁ | R₂ | R₃ |
|---|---|---|---|
| 70 | Br | OCH₃ | Br |
| 72 | NO₂ | OCH₃ | H |
| 73 | I | OCH₃ | I |
| 80 | CH₂Oac | Oac | CH₂OAc |
| 83 | CH₂-piperidine | Oac | CH₂-piperidine |
| 84 | CH₂-diethyl amine | Oac | CH₂-diethyl amine. |

* * * * *